US011345945B2

(12) United States Patent
Davletov et al.

(10) Patent No.: US 11,345,945 B2
(45) Date of Patent: May 31, 2022

(54) STABLE VAMP REPORTER ASSAY

(71) Applicant: THE UNIVERSITY OF SHEFFIELD, Sheffield (GB)

(72) Inventors: Bazbek Davletov, Sheffield (GB); Andrew Alexander Peden, Sheffield (GB); Aleksander Mikael Rudolf Rust, Sheffield (GB); Ciara Louise Doran, Sheffield (GB)

(73) Assignee: The University Of Sheffield, Sheffield (GB)

( * ) Notice: Subject to any disclaimer, the term of this patent is extended or adjusted under 35 U.S.C. 154(b) by 175 days.

(21) Appl. No.: 16/486,408

(22) PCT Filed: Feb. 14, 2018

(86) PCT No.: PCT/GB2018/050397
§ 371 (c)(1),
(2) Date: Aug. 15, 2019

(87) PCT Pub. No.: WO2018/150177
PCT Pub. Date: Aug. 23, 2018

(65) Prior Publication Data
US 2020/0024639 A1 Jan. 23, 2020

(30) Foreign Application Priority Data
Feb. 16, 2017 (GB) ..................... 1702500

(51) Int. Cl.
*C12Q 1/66* (2006.01)
*C07K 14/705* (2006.01)
*C12Q 1/37* (2006.01)

(52) U.S. Cl.
CPC .............. *C12Q 1/66* (2013.01); *C07K 14/705* (2013.01); *C12Q 1/37* (2013.01); *C07K 2319/50* (2013.01); *C07K 2319/61* (2013.01); *C12Y 113/12007* (2013.01)

(58) Field of Classification Search
CPC .............................. C07K 2319/50; C12Q 1/66
See application file for complete search history.

(56) References Cited

U.S. PATENT DOCUMENTS

| 4,683,202 | A | 7/1987 | Mullis |
| 7,094,888 | B2 | 8/2006 | Miesenboeck et al. |
| 2004/0137611 | A1* | 7/2004 | Miesenbock ........... C07K 14/47 435/320.1 |
| 2007/0166332 | A1 | 7/2007 | Steward et al. |
| 2009/0042231 | A1 | 2/2009 | Steward et al. |
| 2013/0065259 | A1 | 3/2013 | Kalkum et al. |
| 2015/0044709 | A1 | 2/2015 | Eisele |

FOREIGN PATENT DOCUMENTS

| WO | 9836081 | 8/1998 |
| WO | 2006095654 | 9/2006 |
| WO | 2011047265 | 4/2011 |
| WO | 2012047325 | 4/2012 |
| WO | 2013050204 | 4/2013 |
| WO | 2015132790 | 9/2015 |
| WO | 2016079310 | 5/2016 |
| WO | 2016127100 | 8/2016 |
| WO | 2017204561 | 11/2017 |

OTHER PUBLICATIONS

Sevlever et al., 2015; Genetically-controlled vesicle-associated membrane protein 1 expression may contribute to Alzheimer's pathophysiology and susceptibility. Molecular Neurodegeneration. 10:18, pp. 1-12.*
Hall et al. 2012; Engineered luciferase reporter from a deep sea shrimp utilizing a novel imidazopyrazinone substrate. ACS Chemical Biology. 7: 1848-1857.*
Yamasaki et al. 1994; Cleavage of members of the synatpobrevin/VAMP family fy types D and F Botulinum neurotoxins and tetanus toxin. Journal of Biological Chemistry. 267(17): 12764-12772.*
Trimble et al. 1988; VAMP-1: a synaptic vesicle—associated integral membrane protein. Proc. Natl. Acad. Sci. 85: 4538-4542.*
Cell-Based VAMP Reporter Assay for Tetanus Vaccine Development, CRACK IT (Technologies for better science), Available Online at: https://crackit.org.uk/cell-basedvamp-reporter-assay-tetanus-vaccine-development, Nov. 2016, 5 pages.
Fernandez-Salas et al., 2012, Botulinum Neurotoxin Serotype a Specific Cell-Based Potency Assay to Replace the Mouse Bioassay, PLOS One, vol. 7, Issue 11, 13 pages.
International Application No. PCT/GB2018/050397, International Preliminary Report on Patentability dated Aug. 29, 2019, 11 pages.
International Application No. PCT/GB2018/050397, International Search Report and Written Opinion dated May 11, 2018, 14 pages.
Miesenboeck et al., 1997, Patterns of Synaptic Activity in Neural Networks Recorded by Light Emission from Synaptolucins, Proceedings of the National Academy of Sciences, vol. 94, No. 7, pp. 3402-3407.
Moghaddam et al., 2010, Cloning and Expression of a Region of Vesicle Associated Membrane Protein2 (VAMP2) Gene and its Use as a Recombinant Peptide Substrate for Assaying Clostridial Neurotoxins in Contaminated Biologicals, Biologicals, Academic Press Ltd., vol. 38, No. 1, pp. 113-119.
Rust et al., 2017, A Cell Line for Detection of Botulinum Neurotoxin Type B, Frontiers in Pharmacology, vol. 8, Article 796, 8 pages.

(Continued)

*Primary Examiner* — Karen Cochrane Carlson
(74) *Attorney, Agent, or Firm* — Kilpatrick Townsend & Stockton LLP

(57) ABSTRACT

The present invention provides a polypeptide comprising an N-terminal polypeptide domain having luciferase activity and a C-terminal polypeptide domain having VAMP1, VAMP2 or VAMP3 activity where VAMP stands for vesicle-associated membrane protein. Corresponding nucleic acid molecules, expression vectors and genetically modified cells are also provided. The invention also provides methods and uses of the same.

20 Claims, 7 Drawing Sheets

Specification includes a Sequence Listing.

(56) References Cited

OTHER PUBLICATIONS

United Kingdom Application No. 1702500.8, Search Report dated Dec. 12, 2017, 9 pages.
"Advisory Committee on the Microbiological Safety of Food", Report on Botulism in Cattle, Available Online at http://acmsf.food.gov.uk/sites/default/files/mnt/drupal_data/sources/files/multimedia/pdfs/botulismincattlereport1206.pdf, 55 pages.
Adams Jr. et al., "Beyond D-Luciferin: Expanding the Scope of Bioluminescence Imaging in Vivo", Current Opinion in Chemical Biology, vol. 21, Aug. 2014, pp. 112-120.
Altschul et al., "Gapped BLAST and PSI-BLAST: A New Generation of Protein Database Search Programs", Nucleic Acids Research, vol. 25, No. 17, Sep. 1, 1997, pp. 3389-3402.
Aslanidis et al., "Ligation-Independent Cloning of PCR Products (LIC-PCR)", Nucleic Acids Research, vol. 18, No. 20, Oct. 25, 1990, pp. 6069-6074.
Beaucage et al., "Deoxynucleoside Phosphoramidites—A New Class of Key Intermediates for Deoxypolynucleotide Synthesis", Tetrahedron Letters, vol. 22, No. 20, Dec. 1981, pp. 1859-1862.
Behrensdorf-Nicol et al., ""BINACLE" Assay for in Vitro Detection of Active Tetanus Neurotoxin in Toxoids", Altex, vol. 32, No. 2, 2015, pp. 137-142.
Bowen et al., "Conformation of the Synaptobrevin Transmembrane Domain", Proceedings of the National Academy of Sciences of the United States of America, vol. 103, No. 22, May 30, 2006, pp. 8378-8383.
Carter et al., "Genomes, Neurotoxins and Biology of Clostridium Botulinum Group I and Group II", Research in Microbiology, vol. 166, No. 4, May 2015, pp. 303-317.
Caruthers et al., "New Chemical Methods for Synthesizing Polynucleotides", Nucleic Acids Research, Symposium Series, No. 7, 1980, pp. 215-223.
Chen et al., "Snare-Mediated Membrane Fusion", Nature Reviews Molecular Cell Biology, vol. 2, No. 2, Feb. 2001, pp. 98-106.
Chen et al., "Substrate Recognition of VAMP-2 by Botulinum Neurotoxin B and Tetanus Neurotoxin", Journal of Biological Chemistry, vol. 283, No. 30, Jul. 25, 2008, pp. 21153-21159.
Cohen et al., "Nonchromosomal Antibiotic Resistance in Bacteria: Genetic Transformation of *Escherichia coli* by R-Factor DNA", Proceedings of the National Academy of Sciences of the United States of America, vol. 69, No. 8, Aug. 1972, pp. 2110-2114.
Darios et al., "SNARE Tagging Allows Stepwise Assembly of a Multimodular Medicinal Toxin", Proceedings of the National Academy of Sciences of the United States of America, vol. 107, No. 42, Oct. 19, 2010, pp. 18197-18201.
Davletov et al., "Beyond BOTOX: Advantages and Limitations of Individual Botulinum Neurotoxins", Trends in Neurosciences, vol. 28, No. 8, Aug. 2005, pp. 446-452.
Doran et al., "Mouse DRG Cell Line With Properties of Nociceptors", PLoS One, vol. 10, No. 6, Jun. 8, 2015, pp. 1-15.
Fasshauer et al., "Conserved Structural Features of the Synaptic Fusion Complex: SNARE Proteins Reclassified as Q- and R-SNAREs", Proceedings of the National Academy of Sciences of the United States of America, vol. 95, No. 26, Dec. 22, 1998, pp. 15781-15786.
Fasshauer et al., "Identification of a Minimal Core of the Synaptic SNARE Complex Sufficient for Reversible Assembly and Disassembly", Biochemistry, vol. 37, No. 29, Jul. 21, 1998, pp. 10354-10362.
Fasshauer et al., "Mixed and Non-Cognate Snare Complexes. Characterization of Assembly and Biophysical Properties", The Journal of Biological Chemistry, vol. 274, No. 22, May 28, 1999, pp. 15440-15446.
Frank et al., "Application of Enzyme Bioluminescence for Medical Diagnostics", Bioluminescence: Fundamentals and Applications in Biotechnology, vol. 1, 2014, pp. 175-197.
Hall et al., "Engineered Luciferase Reporter from a Deep Sea Shrimp Utilizing a Novel Imidazopyrazinone Substrate", ACS Chemical Biology, vol. 7, No. 11, Nov. 16, 2012, pp. 1848-1857.
Horn et al., "Synthesis of oligonucleotides on cellulose. Part II: Design and synthetic strategy to the synthesis of 22 oligodeoxynucleotides coding for gastric inhibitory polypeptide (GIP).", Nucleic Acids Research, Symposium Series No. 7,, 1980, pp. 225-232.
Hoshino, "Current Advanced Bioluminescence Technology in Drug Discovery", Expert Opinion on Drug Discovery, vol. 4, No. 4, Apr. 2009, pp. 373-389.
Hu et al., "Vesicular Restriction of Synaptobrevin Suggests a Role for Calcium in Membrane Fusion", Nature, vol. 415, No. 6872, Feb. 7, 2002, pp. 646-650.
Hubbard et al., "Functional Evaluation of Biological Neurotoxins in Networked Cultures of Stem Cell-Derived Central Nervous System Neurons", Journal of Visualized Experiments: JoVE, vol. 96, Feb. 5, 2015, pp. 1-7.
Jat et al., "Direct Derivation of Conditionally Immortal Cell Lines From an H-2Kb-tsA58 Transgenic Mouse", Proceedings of the National Academy of Sciences of the United States of America, vol. 88, No. 12, Jun. 15, 1991, pp. 5096-5100.
Luchansky et al., "Application of Electroporation for Transfer of Plasmid DNA to *Lactobacillus, Lactococcus, Leuconostoc, Listeria, Pediococcus, Bacillus, Staphylococcus, Enterococcus* and *Propionibacterium*", Molecular Microbiology, vol. 2, No. 5, Sep. 1988, pp. 637-646.
Matthes et al., "Simultaneous Rapid Chemical Synthesis of Over One Hundred Oligonucleotides on a Microscale", The EMBO Journal, vol. 3, No. 4, Apr. 1984, pp. 801-805.
Pellizzari et al., "Tetanus and Botulinum Neurotoxins: Mechanism of Action and Therapeutic Uses", Philosophical Transactions of the Royal Society of London B Biological Sciences, vol. 354, No. 1381, Feb. 28, 1999, pp. 259-268.
Randhawa et al., "VAMP2, but Not VAMP3/Cellubrevin, Mediates Insulin-Dependent Incorporation of GLUT4 Into the Plasma Membrane of L6 Myoblasts", Molecular Biology of the Cell, vol. 11, No. 7, Jul. 2000, pp. 2403-2417.
Saiki et al., "Primer-Directed Enzymatic Amplification of DNA With a Thermostable DNA Polymerase", Science, vol. 239, No. 4839, Jan. 29, 1988, pp. 487-491.
Sambrook et al., "Molecular Cloning: A Laboratory Manual", Second Edition, Cold Spring Harbor Laboratory Press, 1989, 30 pages.
Sesardic, "Bioassays for Evaluation of Medical Products Derived From Bacterial Toxins", Current Opinion in Microbiology, vol. 15, No. 3, 2012, pp. 310-316.
Thorne et al., "Illuminating Insights Into Firefly Luciferase and Other Bioluminescent Reporters Used in Chemical Biology", Chemistry & Biology, vol. 17, No. 6, Jun. 25, 2010, pp. 646-657.
Yamamoto et al., "Specificity of Botulinum Protease for Human VAMP Family Proteins", Microbiology and Immunology, vol. 56, No. 4, Apr. 2012, pp. 245-253.
Japanese Application No. 2019-543949, Office Action dated Dec. 3, 2021, 19 pages.

* cited by examiner

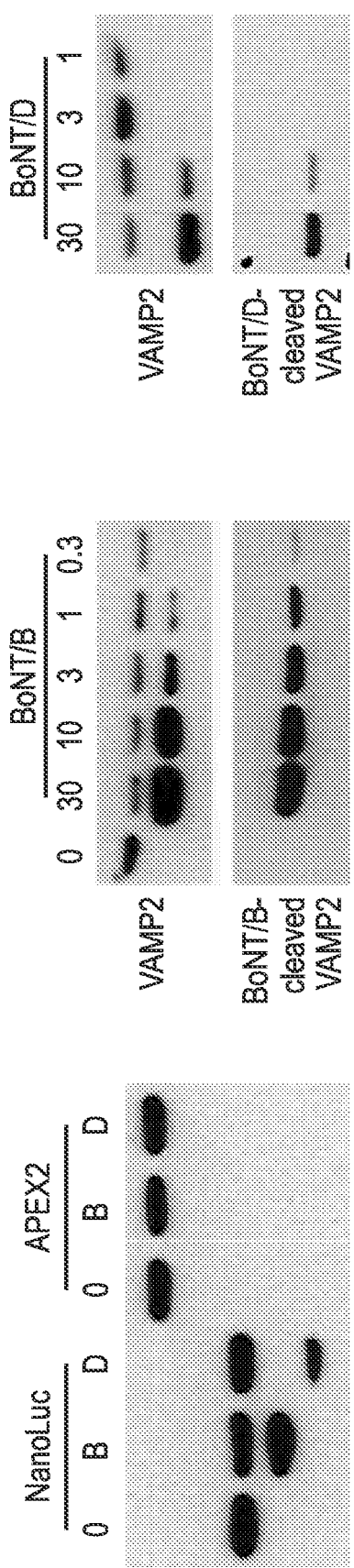
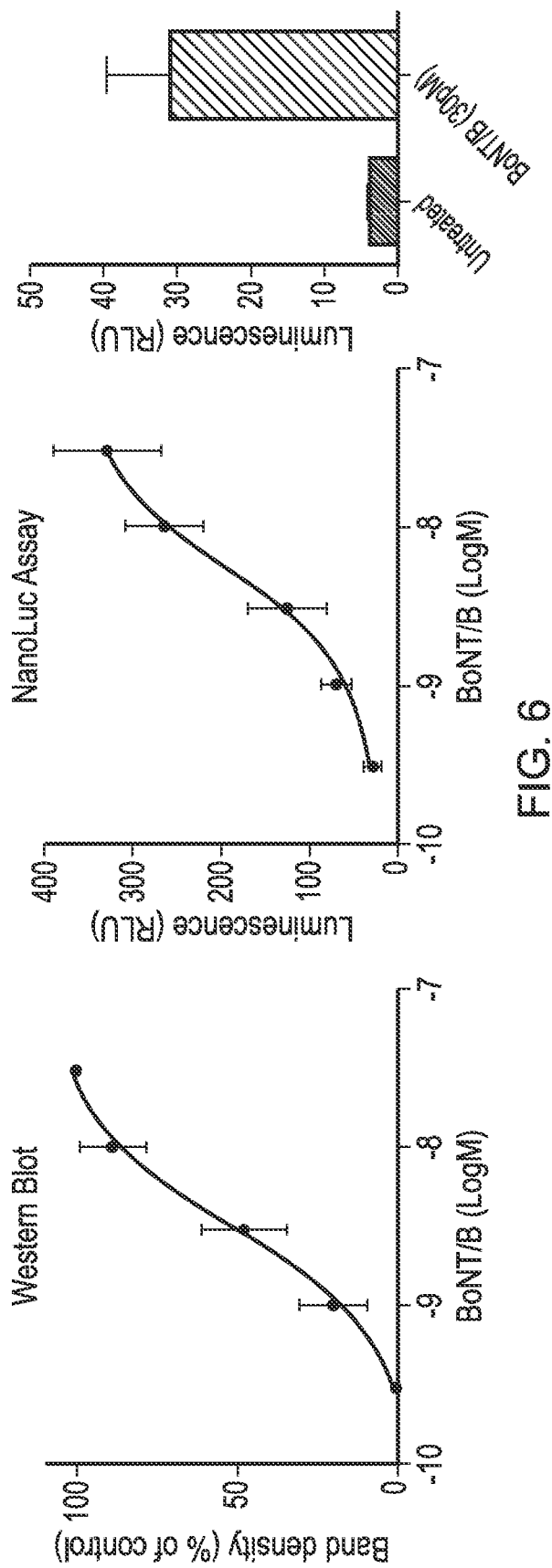
FIG. 4
FIG. 5
FIG. 6

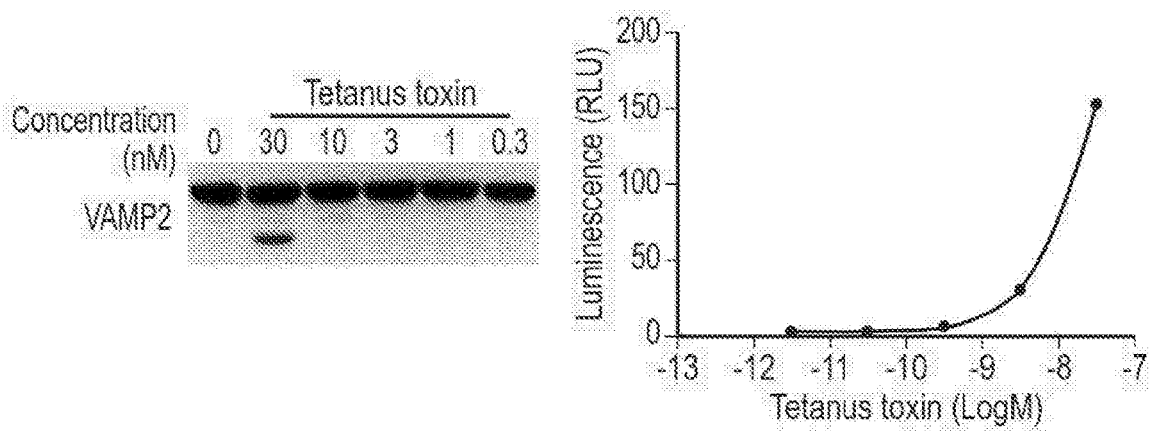

FIG. 7

Human VAMP1 Ref sequence NM_014231.4. (SEQ ID NO:1)
MSAPAQPPAEGTEGTAPGGGPPGPPPNMTSNRRLQQTQAQVEEVVDIIRVNVD
KVLERDQKLSELDDRADALQAGASQFESSAAKLKRKYWWKNCKMMIMLGAICA
IIVVVIVIYFFT

FIG. 8

Human VAMP2 Ref sequence NM_014232.2. (SEQ ID NO:2)
MSATAATAPPAAPAGEGGPPAPPPNLTSNRRLQQTQAQVDEVVDIMRVNVDKV
LERDQKLSELDDRADALQAGASQFETSAAKLKRKYWWKNLKMMIILGVICAII
LIIIIVYFST

FIG. 9

Human VAMP3 Ref sequence NM_004781.3 (SEQ ID NO:3)
MSTGPTAATGSNRRLQQTQNQVDEVVDIMRVNVDKVLERDQKLSELDDRADAL
QAGASQFETSAAKLKRKYWWKNCKMWAIGITVLVIFIIIIVWVSS

FIG. 10

NanoLuc Ref: ACS Chem Biol. 2012 Nov 16; 7(11): 1848–1857. (SEQ ID NO:4)
MVFTLEDFVGDWRQTAGYNLDQVLEQGGVSSLFQNLGVSVTPIQRIVLSGENG
LKIDIHVIIPYEGLSGDQMGQIEKIFKVVYPVDDHHFKVILHYGTLVIDGVTP
NMIDYFGRPYEGIAVFDGKKITVTGTLWNGNKIIDERLINPDGSLLFRVTING
VTGWRLCERILA

FIG. 11

HA-APEX2-VAMP2 DNA Sequence (SEQ ID NO: 5):

GCGGCCGCATGTACCCATACGATGTTCCAGATTACGCT<u>GGAAAGTCTTACCCA
ACTGTGAGTGCTGATTACCAGGACGCCGTTGAGAAGGCGAAGAAGAAGCTCAG
AGGCTTCATCGCTGAGAAGAGATGCGCTCCTCTAATGCTCCGTTTGGCATTCC
ACTCTGCTGGAACCTTTGACAAGGGCACGAAGACCGGTGGACCCTTCGGAACC
ATCAAGCACCCTGCCGAACTGGCTCACAGCGCTAACAACGGTCTTGACATCGC
TGTTAGGCTTTTGGAGCCACTCAAGGCGGAGTTCCCTATTTTGAGCTACGCCG
ATTTCTACCAGTTGGCTGGCGTTGTTGCCGTTGAGGTCACGGGTGGACCTAAG
GTTCCATTCCACCCTGGAAGAGAGGACAAGCCTGAGCCACCACCAGAGGGTCG
CTTGCCCGATCCCACTAAGGGTTCTGACCATTTGAGAGATGTGTTTGGCAAAG
CTATGGGGCTTACTGACCAAGATATCGTTGCTCTATCTGGGGGTCACACTATT
GGAGCTGCACACAAGGAGCGTTCTGGATTTGAGGGTCCCTGGACCTCTAATCC
TCTTATTTTCGACAACTCATACTTCACGGAGTTGTTGAGTGGTGAGAAGGAAG
GTCTCCTTCAGCTACCTTCTGACAAGGCTCTTTTGTCTGACCCTGTATTCCGC
CCTCTCGTTGACAAATATGCAGCGGACGAAGATGCCTTCTTTGCTGATTACGC
TGAGGCTCACCAAAAGCTTTCCGAGCTTGGGTTTGCTGATGCCCTGCAGCTGC
CTCCCCTGGAGCGCCTGACCCTGGAC</u>*GGACCCGGACCCGGACCC*atgtctgct
accgctgccacggccccccctgctgcccggctggggagggtggtccccctgc
accccctccaaacctcaccagtaacaggagactgcagcagacccaggcccagg
tggatgaggtggtggacatcatgagggtgaacgtggacaaggtcctggagcga
gaccagaagctgtcggagctggacgaccgtgcagatgcactccaggcggggc
ctcccagtttgaaacaagcgcagccaagctcaagcgcaaatactggtggaaaa
acctcaagatgatgatcatcttgggagtgatttgcgccatcatcctcatcatc
atcatagtttacttcagcacttaaGAATTC

Bold=HA-tag
<u>Underscore</u>=APEX2
*Italics*=Proline Glycine linker
Lowercase=Human VAMP2 (NM_014232)
Gray=restriction sites

FIG. 12

HA-NanoLuc-VAMP2 DNA Sequence (SEQ ID NO: 6):

GCGGCCGCATGTACCCATACGATGTTCCAGATTACGCT<u>GTCTTCACACTCGAA</u>
<u>GATTTCGTTGGGGACTGGCGACAGACAGCCGGCTACAACCTGGACCAAGTCCT</u>
<u>TGAACAGGGAGGTGTGTCCAGTTTGTTTCAGAATCTCGGGGTGTCCGTAACTC</u>
<u>CGATCCAAAGGATTGTCCTGAGCGGTGAAAATGGGCTGAAGATCGACATCCAT</u>
<u>GTCATCATCCCGTATGAAGGTCTGAGCGGCGACCAAATGGGCCAGATCGAAAA</u>
<u>AATTTTTAAGGTGGTGTACCCTGTGGATGATCATCACTTTAAGGTGATCCTGC</u>
<u>ACTATGGCACACTGGTAATCGACGGGGTTACGCCGAACATGATCGACTATTTC</u>
<u>GGACGGCCGTATGAAGGCATCGCCGTGTTCGACGGCAAAAAGATCACTGTAAC</u>
<u>AGGGACCCTGTGGAACGGCAACAAAATTATCGACGAGCGCCTGATCAACCCCG</u>
<u>ACGGCTCCCTGCTGTTCCGAGTAACCATCAACGGAGTGACCGGCTGGCGGCTG</u>
<u>TGCGAACGCATTCTGGCG</u>*GGACCCGGACCCGGACCC*atgtctgctaccgctgc
cacggccccccctgctgccccggctggggagggtggtcccctgcaccccctc
caaacctcaccagtaacaggagactgcagcagacccaggcccaggtggatgag
gtggtggacatcatgagggtgaacgtggacaaggtcctggagcgagaccagaa
gctgtcggagctggacgaccgtgcagatgcactccaggcggggcctcccagt
ttgaaacaagcgcagccaagctcaagcgcaaatactggtggaaaaacctcaag
atgatgatcatcttgggagtgatttgcgccatcatcctcatcatcatcatagt
ttacttcagcacttaaGAATTC

Bold=HA-tag
<u>Underscore</u>= NanoLuc
*Italics*=Proline Glycine linker
Lowercase=Human VAMP2 (NM_014232)
Gray=restriction sites

Human VAMP1 core sequence (SEQ ID NO:7)

QVEEVVDIIRVNVDKVLERDQKLSELDDRADALQAGASQFESSAAKLKRKYWW
KNCKMMIMLGAICAIIVVVIVIYFFT

FIG. 15

Human VAMP2 core sequence (SEQ ID NO:8)

QVDEVVDIMRVNVDKVLERDQKLSELDDRADALQAGASQFETSAAKLKRKYWW
KNLKMMIILGVICAIILIIIVYFST

FIG. 16

Human VAMP3 core sequence (SEQ ID NO:9)

QVDEVVDIMRVNVDKVLERDQKLSELDDRADALQAGASQFETSAAKLKRKYWW
KNCKMWAIGITVLVIFIIIIVWVVSS

FIG. 17

SEQUENCE LISTING

<160> NUMBER OF SEQ ID NOS: 24

<210> SEQ ID NO 1
<211> LENGTH: 118
<212> TYPE: PRT
<213> ORGANISM: Homo sapiens

<400> SEQUENCE: 1

```
Met Ser Ala Pro Ala Gln Pro Pro Ala Glu Gly Thr Glu Gly Thr Ala
1               5                   10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Ile
        35                  40                  45
```

```
Arg Val Asn Val Asp Lys Val Leu Glu Arg Asp Gln Lys Leu Ser Glu
        50                  55                  60
Leu Asp Asp Arg Ala Asp Ala Leu Gln Ala Gly Ala Ser Gln Phe Glu
65                  70                  75                  80
Ser Ser Ala Ala Lys Leu Lys Arg Lys Tyr Trp Trp Lys Asn Cys Lys
                85                  90                  95
Met Met Ile Met Leu Gly Ala Ile Cys Ala Ile Ile Val Val Val Ile
            100                 105                 110
Val Ile Tyr Phe Phe Thr
            115
```

<210> SEQ ID NO 2
<211> LENGTH: 116
<212> TYPE: PRT
<213> ORGANISM: Homo sapiens

<400> SEQUENCE: 2

```
Met Ser Ala Thr Ala Ala Thr Ala Pro Pro Ala Ala Pro Ala Gly Glu
1               5                   10                  15
Gly Gly Pro Pro Ala Pro Pro Pro Asn Leu Thr Ser Asn Arg Arg Leu
            20                  25                  30
Gln Gln Thr Gln Ala Gln Val Asp Glu Val Val Asp Ile Met Arg Val
        35                  40                  45
Asn Val Asp Lys Val Leu Glu Arg Asp Gln Lys Leu Ser Glu Leu Asp
    50                  55                  60
Asp Arg Ala Asp Ala Leu Gln Ala Gly Ala Ser Gln Phe Glu Thr Ser
65                  70                  75                  80
Ala Ala Lys Leu Lys Arg Lys Tyr Trp Trp Lys Asn Leu Lys Met Met
                85                  90                  95
Ile Ile Leu Gly Val Ile Cys Ala Ile Ile Leu Ile Ile Ile Ile Val
            100                 105                 110
Tyr Phe Ser Thr
            115
```

<210> SEQ ID NO 3
<211> LENGTH: 100
<212> TYPE: PRT
<213> ORGANISM: Homo sapiens

<400> SEQUENCE: 3

```
Met Ser Thr Gly Pro Thr Ala Ala Thr Gly Ser Asn Arg Arg Leu Gln
1               5                   10                  15
Gln Thr Gln Asn Gln Val Asp Glu Val Val Asp Ile Met Arg Val Asn
            20                  25                  30
Val Asp Lys Val Leu Glu Arg Asp Gln Lys Leu Ser Glu Leu Asp Asp
        35                  40                  45
Arg Ala Asp Ala Leu Gln Ala Gly Ala Ser Gln Phe Glu Thr Ser Ala
    50                  55                  60
Ala Lys Leu Lys Arg Lys Tyr Trp Trp Lys Asn Cys Lys Met Trp Ala
65                  70                  75                  80
Ile Gly Ile Thr Val Leu Val Ile Phe Ile Ile Ile Ile Ile Val Trp
                85                  90                  95
Val Val Ser Ser
            100
```

<210> SEQ ID NO 4
<211> LENGTH: 171

```
<212> TYPE: PRT
<213> ORGANISM: Artificial Sequence
<220> FEATURE:
<223> OTHER INFORMATION: NanoLuc Ref: ACS Chem Biol. 2012 Nov 16; 7(11):
      1848-1857

<400> SEQUENCE: 4

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 5
<211> LENGTH: 1196
<212> TYPE: DNA
<213> ORGANISM: Artificial Sequence
<220> FEATURE:
<223> OTHER INFORMATION: HA-APEX2-VAMP2 sequence

<400> SEQUENCE: 5
gcggccgcat gtacccatac gatgttccag attacgctgg aaagtcttac ccaactgtga    60
gtgctgatta ccaggacgcc gttgagaagg cgaagaagaa gctcagaggc ttcatcgctg   120
agaagagatg cgctcctcta atgctccgtt tggcattcca ctctgctgga acctttgaca   180
agggcacgaa gaccggtgga cccttcggaa ccatcaagca cctgccgaa ctggctcaca   240
gcgctaacaa cggtcttgac atcgctgtta ggcttttgga gccactcaag gcggagttcc   300
ctatttgag ctacgccgat ttctaccagt tggctggcgt tgttgccgtt gaggtcacgg   360
gtggacctaa ggttccattc caccctggaa gagaggacaa gcctgagcca ccaccagagg   420
gtcgcttgcc cgatcccact aagggttctg accatttgag agatgtgttt ggcaaagcta   480
tggggcttac tgaccaagat atcgttgctc tatctggggg tcacactatt ggagctgcac   540
acaaggagcg ttctggattt gagggtccct ggacctctaa tcctcttatt ttcgacaact   600
catacttcac ggagttgttg agtggtgaga aggaaggtct ccttcagcta ccttctgaca   660
aggctctttt gtctgaccct gtattccgcc ctctcgttga caaatatgca gcggacgaag   720
atgccttctt tgctgattac gctgaggctc accaaaagct tccgagctt gggtttgctg   780
atgccctgca gctgcctccc ctggagcgcc tgaccctgga cggaccggga cccgacccca   840
```

| | |
|---|---|
| tgtctgctac cgctgccacg gcccccctg ctgccccggc tggggagggt ggtcccctg | 900 |
| cacccctcc aaacctcacc agtaacagga gactgcagca gacccaggcc caggtggatg | 960 |
| aggtggtgga catcatgagg gtgaacgtgg acaaggtcct ggagcgagac cagaagctgt | 1020 |
| cggagctgga cgaccgtgca gatgcactcc aggcgggggc ctcccagttt gaaacaagcg | 1080 |
| cagccaagct caagcgcaaa tactggtgga aaaacctcaa gatgatgatc atcttgggag | 1140 |
| tgatttgcgc catcatcctc atcatcatca tagtttactt cagcacttaa gaattc | 1196 |

<210> SEQ ID NO 6
<211> LENGTH: 923
<212> TYPE: DNA
<213> ORGANISM: Artificial Sequence
<220> FEATURE:
<223> OTHER INFORMATION: HA-NanoLuc-VAMP2 sequence

<400> SEQUENCE: 6

| | |
|---|---|
| gcggccgcat gtacccatac gatgttccag attacgctgt cttcacactc gaagatttcg | 60 |
| ttggggactg gcgacagaca gccggctaca acctggacca agtccttgaa cagggaggtg | 120 |
| tgtccagttt gtttcagaat ctcggggtgt ccgtaactcc gatccaaagg attgtcctga | 180 |
| gcggtgaaaa tgggctgaag atcgacatcc atgtcatcat cccgtatgaa ggtctgagcg | 240 |
| gcgaccaaat gggccagatc gaaaaaattt ttaaggtggt gtaccctgtg gatgatcatc | 300 |
| actttaaggt gatcctgcac tatggcacac tggtaatcga cggggttacg ccgaacatga | 360 |
| tcgactattt cggacggccg tatgaaggca tcgccgtgtt cgacggcaaa aagatcactg | 420 |
| taacagggac cctgtggaac ggcaacaaaa ttatcgacga gcgcctgatc aaccccgacg | 480 |
| gctccctgct gttccgagta accatcaacg gagtgaccgg ctggcggctg tgcgaacgca | 540 |
| ttctggcggg accggacccc ggacccatgt ctgctaccgc tgccacggcc cccctgctg | 600 |
| ccccggctgg ggagggtggt ccccctgcac cccctccaaa cctcaccagt aacaggagac | 660 |
| tgcagcagac ccaggcccag gtggatgagg tggtggacat catgagggtg aacgtggaca | 720 |
| aggtcctgga gcgagaccag aagctgtcgg agctggacga ccgtgcagat gcactccagg | 780 |
| cggggggcctc ccagtttgaa acaagcgcag ccaagctcaa gcgcaaatac tggtggaaaa | 840 |
| acctcaagat gatgatcatc ttgggagtga tttgcgccat catcctcatc atcatcatag | 900 |
| tttacttcag cacttaagaa ttc | 923 |

<210> SEQ ID NO 7
<211> LENGTH: 79
<212> TYPE: PRT
<213> ORGANISM: Homo sapiens

<400> SEQUENCE: 7

Gln Val Glu Glu Val Val Asp Ile Ile Arg Val Asn Val Asp Lys Val
1               5                   10                  15

Leu Glu Arg Asp Gln Lys Leu Ser Glu Leu Asp Asp Arg Ala Asp Ala
            20                  25                  30

Leu Gln Ala Gly Ala Ser Gln Phe Glu Ser Ser Ala Ala Lys Leu Lys
        35                  40                  45

Arg Lys Tyr Trp Trp Lys Asn Cys Lys Met Met Ile Met Leu Gly Ala
    50                  55                  60

Ile Cys Ala Ile Ile Val Val Val Ile Val Ile Tyr Phe Phe Thr
65                  70                  75

<210> SEQ ID NO 8

```
<211> LENGTH: 79
<212> TYPE: PRT
<213> ORGANISM: Homo sapiens

<400> SEQUENCE: 8

Gln Val Asp Glu Val Val Asp Ile Met Arg Val Asn Val Asp Lys Val
1               5                   10                  15

Leu Glu Arg Asp Gln Lys Leu Ser Glu Leu Asp Asp Arg Ala Asp Ala
            20                  25                  30

Leu Gln Ala Gly Ala Ser Gln Phe Glu Thr Ser Ala Ala Lys Leu Lys
        35                  40                  45

Arg Lys Tyr Trp Trp Lys Asn Leu Lys Met Met Ile Ile Leu Gly Val
    50                  55                  60

Ile Cys Ala Ile Ile Leu Ile Ile Ile Val Tyr Phe Ser Thr
65                  70                  75

<210> SEQ ID NO 9
<211> LENGTH: 80
<212> TYPE: PRT
<213> ORGANISM: Homo sapiens

<400> SEQUENCE: 9

Gln Val Asp Glu Val Val Asp Ile Met Arg Val Asn Val Asp Lys Val
1               5                   10                  15

Leu Glu Arg Asp Gln Lys Leu Ser Glu Leu Asp Asp Arg Ala Asp Ala
            20                  25                  30

Leu Gln Ala Gly Ala Ser Gln Phe Glu Thr Ser Ala Ala Lys Leu Lys
        35                  40                  45

Arg Lys Tyr Trp Trp Lys Asn Cys Lys Met Trp Ala Ile Gly Ile Thr
    50                  55                  60

Val Leu Val Ile Phe Ile Ile Ile Ile Val Trp Val Ser Ser
65                  70                  75                  80

<210> SEQ ID NO 10
<211> LENGTH: 8
<212> TYPE: PRT
<213> ORGANISM: Artificial Sequence
<220> FEATURE:
<223> OTHER INFORMATION: Anti-BoNT/B cleaved VAMP2 sequence

<400> SEQUENCE: 10

Ala Leu Gln Ala Gly Ala Ser Gln
1               5

<210> SEQ ID NO 11
<211> LENGTH: 8
<212> TYPE: PRT
<213> ORGANISM: Artificial Sequence
<220> FEATURE:
<223> OTHER INFORMATION: anti-BoNT/D cleaved VAMP2 sequence

<400> SEQUENCE: 11

Lys Val Leu Glu Arg Asp Gln Lys
1               5

<210> SEQ ID NO 12
<211> LENGTH: 8
<212> TYPE: PRT
<213> ORGANISM: Artificial Sequence
<220> FEATURE:
<223> OTHER INFORMATION: BoNT/B TeNT VAMP 1 cleavage site sequence
<220> FEATURE:
<221> NAME/KEY: MISC_FEATURE
```

```
<222> LOCATION: (4)..(4)
<223> OTHER INFORMATION: position 78 in longer sequence

<400> SEQUENCE: 12

Gly Ala Ser Gln Phe Glu Ser Ser
1               5

<210> SEQ ID NO 13
<211> LENGTH: 8
<212> TYPE: PRT
<213> ORGANISM: Artificial Sequence
<220> FEATURE:
<223> OTHER INFORMATION: BoNT/B TeNT VAMP 2 cleavage site sequence
<220> FEATURE:
<221> NAME/KEY: MISC_FEATURE
<222> LOCATION: (4)..(4)
<223> OTHER INFORMATION: position 76 in longer sequence

<400> SEQUENCE: 13

Gly Ala Ser Gln Phe Glu Thr Ser
1               5

<210> SEQ ID NO 14
<211> LENGTH: 8
<212> TYPE: PRT
<213> ORGANISM: Artificial Sequence
<220> FEATURE:
<223> OTHER INFORMATION: BoNT/B  TeNT VAMP3 cleavage site sequence
<220> FEATURE:
<221> NAME/KEY: MISC_FEATURE
<222> LOCATION: (4)..(4)
<223> OTHER INFORMATION: position 59 in longer sequence

<400> SEQUENCE: 14

Gly Ala Ser Gln Phe Glu Thr Ser
1               5

<210> SEQ ID NO 15
<211> LENGTH: 8
<212> TYPE: PRT
<213> ORGANISM: Artificial Sequence
<220> FEATURE:
<223> OTHER INFORMATION: BoNT/D VAMP1 cleavage site sequence
<220> FEATURE:
<221> NAME/KEY: MISC_FEATURE
<222> LOCATION: (4)..(4)
<223> OTHER INFORMATION: position 61 in longer sequence

<400> SEQUENCE: 15

Arg Asp Gln Lys Leu Ser Glu Leu
1               5

<210> SEQ ID NO 16
<211> LENGTH: 8
<212> TYPE: PRT
<213> ORGANISM: Artificial Sequence
<220> FEATURE:
<223> OTHER INFORMATION: BoNT/D VAMP2 cleavage site sequence
<220> FEATURE:
<221> NAME/KEY: MISC_FEATURE
<222> LOCATION: (4)..(4)
<223> OTHER INFORMATION: position 59 in longer sequence

<400> SEQUENCE: 16

Arg Asp Gln Lys Leu Ser Glu Leu
1               5

<210> SEQ ID NO 17
<211> LENGTH: 8
```

```
<212> TYPE: PRT
<213> ORGANISM: Artificial Sequence
<220> FEATURE:
<223> OTHER INFORMATION: BoNT/D VAMP3  cleavage site sequence
<220> FEATURE:
<221> NAME/KEY: MISC_FEATURE
<222> LOCATION: (4)..(4)
<223> OTHER INFORMATION: position 42 in longer sequence

<400> SEQUENCE: 17

Arg Asp Gln Lys Leu Ser Glu Leu
1               5

<210> SEQ ID NO 18
<211> LENGTH: 8
<212> TYPE: PRT
<213> ORGANISM: Artificial Sequence
<220> FEATURE:
<223> OTHER INFORMATION: BoNT/F VAMP1  cleavage site sequence
<220> FEATURE:
<221> NAME/KEY: MISC_FEATURE
<222> LOCATION: (4)..(4)
<223> OTHER INFORMATION: position 60 in longer sequence

<400> SEQUENCE: 18

Glu Arg Asp Gln Lys Leu Ser Glu
1               5

<210> SEQ ID NO 19
<211> LENGTH: 8
<212> TYPE: PRT
<213> ORGANISM: Artificial Sequence
<220> FEATURE:
<223> OTHER INFORMATION: BoNT/F VAMP 2  cleavage site sequence
<220> FEATURE:
<221> NAME/KEY: MISC_FEATURE
<222> LOCATION: (4)..(4)
<223> OTHER INFORMATION: position 58 in longer sequence

<400> SEQUENCE: 19

Glu Arg Asp Gln Lys Leu Ser Glu
1               5

<210> SEQ ID NO 20
<211> LENGTH: 8
<212> TYPE: PRT
<213> ORGANISM: Artificial Sequence
<220> FEATURE:
<223> OTHER INFORMATION: BoNT/F VAMP3  cleavage site sequence
<220> FEATURE:
<221> NAME/KEY: MISC_FEATURE
<222> LOCATION: (4)..(4)
<223> OTHER INFORMATION: position 41 in longer sequence

<400> SEQUENCE: 20

Glu Arg Asp Gln Lys Leu Ser Glu
1               5

<210> SEQ ID NO 21
<211> LENGTH: 8
<212> TYPE: PRT
<213> ORGANISM: Artificial Sequence
<220> FEATURE:
<223> OTHER INFORMATION: BoNT/G VAMP 1  cleavage site sequence
<220> FEATURE:
<221> NAME/KEY: MISC_FEATURE
<222> LOCATION: (4)..(4)
<223> OTHER INFORMATION: position 83 in longer sequence

<400> SEQUENCE: 21
```

-continued

```
Glu Ser Ser Ala Ala Lys Leu Lys
1               5

<210> SEQ ID NO 22
<211> LENGTH: 8
<212> TYPE: PRT
<213> ORGANISM: Artificial Sequence
<220> FEATURE:
<223> OTHER INFORMATION: BoNT/G VAMP2  cleavage site sequence
<220> FEATURE:
<221> NAME/KEY: MISC_FEATURE
<222> LOCATION: (4)..(4)
<223> OTHER INFORMATION: position 81 in longer sequence

<400> SEQUENCE: 22

Glu Thr Ser Ala Ala Lys Leu Lys
1               5

<210> SEQ ID NO 23
<211> LENGTH: 8
<212> TYPE: PRT
<213> ORGANISM: Artificial Sequence
<220> FEATURE:
<223> OTHER INFORMATION: BoNT/G VAMP3  cleavage site sequence
<220> FEATURE:
<221> NAME/KEY: MISC_FEATURE
<222> LOCATION: (4)..(4)
<223> OTHER INFORMATION: position 64 in longer sequence

<400> SEQUENCE: 23

Glu Thr Ser Ala Ala Lys Leu Lys
1               5

<210> SEQ ID NO 24
<211> LENGTH: 6
<212> TYPE: PRT
<213> ORGANISM: Artificial Sequence
<220> FEATURE:
<223> OTHER INFORMATION: BoNT/B-cleaved end  VAMP 2  cleavage site
      sequence
<220> FEATURE:
<221> NAME/KEY: MISC_FEATURE
<222> LOCATION: (6)..(6)
<223> OTHER INFORMATION: position 76 in longer sequence

<400> SEQUENCE: 24

Gln Ala Gly Ala Ser Gln
1               5
```

STABLE VAMP REPORTER ASSAY

The present invention provides a polypeptide comprising an N-terminal polypeptide domain having luciferase activity and a C-terminal polypeptide domain having VAMP1, VAMP2 or VAMP3 activity where VAMP stands for vesicle-associated membrane protein. Corresponding nucleic acid molecules, expression vectors and genetically modified cells are also provided. The invention also provides methods and uses of the same.

BACKGROUND

Tetanus is an acute, toxin-mediated disease caused by the bacterium *Clostridium tetani*. Under favourable anaerobic conditions, such as in necrotic wounds, this ubiquitous bacillus can produce tetanus toxin, an extremely potent neurotoxin. Tetanus neurotoxin (also referred to as "TeNT" or "TNx" herein) blocks inhibitory neurotransmission in the central nervous system, resulting in characteristic muscular stiffness and spasms (1). The case-fatality rates are high even where modern intensive care is available (up to 80%).

Tetanus and related botulinum neurotoxins (BoNTs) are large multidomain proteins that bind neurons with high avidity, primarily due to their interaction with neuron-specific gangliosides and proteins (1,5). This binding is mediated by a 50 kDa binding domain which is structurally separated from the effector parts. Following neuronal binding, the neurotoxins are internalised into endocytic vesicles where due to acidification they undergo a conformational change. This pH-triggered structural change allows release of a protease, also known as light chain, into the cytosol where the proteolytic target resides. The specific proteolytic target will depend on the specific neurotoxin, with tetanus neurotoxin, botulinum neurotoxin type B, botulinum neurotoxin type D, botulinum neurotoxin type F and botulinum neurotoxin type G all cleaving vesicle associated membrane proteins (VAMPs) 1, 2 and 3 (albeit at distinct cleavage sites).

VAMPs 1, 2 and 3 are essential for neurotransmission and their cleavage results in a blockade of secretion of neurotransmitters, which could lead to death (1,5). As an example, VAMP2 cleavage leads to a potent blockade of neurotransmitter release with ensuing neuromuscular paralysis. Unfortunately, cleaved VAMP2 is degraded very quickly by unknown intraneuronal mechanisms and thus detection of the cleaved VAMP2 molecule is virtually impossible.

In both humans and managed animals, tetanus is prevented through immunisation with vaccines containing tetanus toxoid, a detoxified form of the TeNT. Tetanus toxoids are prepared from TeNT by detoxifying it with formaldehyde, without destroying their immunising property. The production of tetanus vaccines includes (i) production of TeNT, (ii) chemical inactivation of TeNT and (iii) testing residual TeNT activity (2). The method of production is such that the toxoid should not revert to toxin.

Testing for residual neurotoxin activity is essential throughout the production of tetanus vaccines. The traditional tools used to assess tetanus product safety have changed little over many decades and the assessment still relies on rodent bioassays with lethal effects associated with neuromuscular paralysis. In accordance with WHO guidelines, each new toxoid batch must be tested in guinea pigs or mice for residual TeNT paralytic activity (2). Animal safety testing is expensive, laborious and time-consuming (3,4). Even after vaccine production, additional rodent bioassay tests are conducted on storage properties of tetanus vaccines for possible reversion of TeNT activity. Considering that WHO recently announced its goal of complete anti-tetanus coverage of human population reaching 8 billion, novel, advanced and more efficient methods are needed for the production and evaluation of tetanus toxoids.

Whereas pan-human immunisation with tetanus toxoids is already on WHO objective, many domesticated animals are routinely immunised against not only tetanus but also botulinum type D (6). Botulinum vaccines must also be tested during development to determine if there is any residual neurotoxin activity. As for tetanus vaccines, rodent bioassays are routinely used to assess botulinum vaccine safety.

There is a need for novel animal replacement assays for testing tetanus and botulinum toxoids for residual neurotoxin activity. Furthermore, botulinum neurotoxin type B is an approved medicine which necessitates its potency testing. It is generally agreed that an animal-replacement assay should account for all three steps of neurotoxin action: cell surface binding, internalisation and substrate (e.g. VAMP2) cleavage. To date two major problems have hindered the development of such cell-based assays: the lack of continuous cell lines which bind tetanus and botulinum neurotoxins robustly, and the rapid degradation of the cleaved products (thereby precluding detection of the product of neurotoxin action).

BRIEF SUMMARY OF THE DISCLOSURE

The inventors have developed a novel reporter molecule that comprises an N-terminal polypeptide domain having luciferase activity and a C-terminal polypeptide domain having VAMP1, VAMP2 or VAMP3 activity. The reporter molecule is capable of being cleaved by tetanus neurotoxin, botulinum neurotoxin type B, botulinum neurotoxin type D, botulinum neurotoxin type F and/or botulinum neurotoxin type G (and modified versions thereof, including chimeras, that retain neurotoxin activity). Cleavage of the reporter molecule generates two cleavage products; a first fragment that comprises the N-terminal polypeptide domain having luciferase activity and a portion of the polypeptide domain having VAMP1, VAMP2 or VAMP3 activity; and a second fragment comprising the remaining portion of the polypeptide domain having VAMP1, VAMP2 or VAMP3 activity. Surprisingly, the N-terminal polypeptide domain having luciferase activity reduces or prevents intracellular degradation of the first fragment. Advantageously, the novel reporter molecule therefore provides a new mechanism for quantitative measurement of neurotoxin activity.

The inventors have exemplified the invention by generating a novel nucleic acid molecule that encodes a novel reporter molecule comprising an N-terminal luciferase polypeptide attached to a C-terminal VAMP2 polypeptide. The nucleic acid molecule was expressed in a genetically modified SiMa neuroblastoma cell line. The cells were cultured in the presence of an appropriate botulinum or tetanus neurotoxin and neurotoxin-induced cleavage of the reporter molecule was studied. Surprisingly, neurotoxin-induced cleavage of the novel reporter molecule could be detected quantitatively, due to reduced degradation of the cleavage products.

The function, structure and neurotoxin cleavage sites of VAMP1, VAMP2 and VAMP3 are very similar and highly conserved. Therefore, although the invention was exemplified using a novel reporter construct comprising a C-terminal VAMP2 polypeptide domain (i.e. a polypeptide domain having VAMP2 activity), the invention applies equally to reporter constructs in which the polypeptide domain having VAMP2 activity is replaced with a polypeptide domain having VAMP1 or VAMP3 activity.

Nucleic acid molecules and expression vectors encoding such polypeptides are also provided herein. The nucleic acid molecules and/or expression vectors may be present within any appropriate host cell (i.e. a genetically modified cell).

In one aspect, the invention provides a polypeptide comprising an N-terminal polypeptide domain having luciferase activity and a C-terminal polypeptide domain having VAMP1, VAMP2 or VAMP3 activity.

Suitably, the polypeptide domain having VAMP2 activity comprises the amino acid sequence of SEQ ID NO:8 or SEQ ID NO: 2, or a conservative amino acid sequence variant thereof.

Suitably, the polypeptide domain having VAMP1 activity comprises the amino acid sequence of SEQ ID NO: 7 or SEQ ID NO: 1, or a conservative amino acid sequence variant thereof.

Suitably, the polypeptide domain having VAMP3 activity comprises the amino acid sequence of SEQ ID NO:9 or SEQ ID NO: 3, or a conservative amino acid sequence variant thereof.

Suitably, the polypeptide domain having luciferase activity comprises the amino acid sequence of SEQ ID NO: 4 or a conservative amino acid sequence variant thereof.

In one aspect, the invention provides a nucleic acid molecule encoding a polypeptide according to the invention.

In one aspect, the invention provides an expression vector comprising a nucleic acid molecule according to the invention.

In one aspect, the invention provides a genetically modified cell comprising a nucleic acid molecule according to the invention, or an expression vector according to the invention.

Suitably, the genetically modified cell is selected from the group consisting of a SiMa neuroblastoma cell, a LAN5 neuroblastoma cell, a NG108 neuroblastoma cell, an immortalised neuron and a primary neuron.

In one aspect, the invention provides the use of a polypeptide, nucleic acid molecule, expression vector, or genetically modified cell according to the invention for the detection of neurotoxin activity, wherein the neurotoxin activity is selected from the group consisting of: tetanus neurotoxin activity, botulinum type B neurotoxin activity, botulinum type D neurotoxin activity, botulinum type F neurotoxin activity and botulinum type G neurotoxin activity, or any combination thereof.

Suitably, the neurotoxin activity is detected in a test sample comprising a drug product, a food sample, a clinical sample, an environmental sample or any combination thereof.

Suitably, the neurotoxin activity is detected in a test sample comprising a tetanus toxoid or a botulinum toxoid, or a combination thereof.

Suitably, the neurotoxin activity is detected in a test sample comprising tetanus neurotoxin, botulinum neurotoxin type B, botulinum neurotoxin type D, botulinum neurotoxin type F or botulinum neurotoxin type G, or any combination thereof. The test sample may comprise naturally occurring neurotoxin(s) and/or modified (e.g. artificially modified, including chimeras) versions thereof.

In one aspect, the invention provides a method of detecting neurotoxin activity in a test sample, the method comprising:

(a) culturing a genetically modified cell according to the invention under conditions that allow for expression of a polypeptide comprising an N-terminal polypeptide domain having luciferase activity and a C-terminal polypeptide having VAMP1, VAMP2 or VAMP3 activity;

(b) culturing the cell of (a) in the presence of the test sample under conditions that allow for neurotoxin-induced cleavage of the polypeptide comprising an N-terminal polypeptide domain having luciferase activity and a C-terminal polypeptide having VAMP1, VAMP2 or VAMP3 activity; and (c) determining the level of neurotoxin-induced cleavage of the polypeptide, wherein detection of neurotoxin-induced cleavage of the polypeptide is indicative of neurotoxin activity; wherein the neurotoxin activity is selected from the group consisting of: tetanus neurotoxin activity, botulinum type B neurotoxin activity, botulinum type D neurotoxin activity, botulinum type F neurotoxin activity and botulinum type G neurotoxin activity, or any combination thereof.

Suitably, culturing steps (a) and (b) are carried out simultaneously.

Suitably, the test sample is provided in culture medium.

Suitably, the neurotoxin-induced cleavage of the polypeptide is detected by ELISA, immunoblot, or live cell imaging.

Suitably, the test sample comprises a drug product, a food sample, a clinical sample, an environmental sample or any combination thereof.

Suitably, the test sample comprises a tetanus toxoid or a botulinum toxoid, or a combination thereof.

Suitably, the test sample comprises tetanus neurotoxin, botulinum neurotoxin type B, botulinum neurotoxin type D, botulinum neurotoxin type F, or botulinum neurotoxin type G or any combination thereof. The test sample may comprise naturally occurring neurotoxin(s) and/or modified (e.g. artificially modified, including chimeras) versions thereof.

In one aspect, the invention provides a kit for detecting neurotoxin activity, the kit comprising:

(a) a nucleic acid molecule encoding a polypeptide comprising an N-terminal polypeptide domain having luciferase activity and a C-terminal polypeptide domain having VAMP1, VAMP2 or VAMP3 activity; and (b) a positive control for detecting neurotoxin activity, wherein the positive control is capable of cleaving the polypeptide encoded by the nucleic acid molecule of (a).

The neurotoxin activity may be selected from the group consisting of: tetanus neurotoxin activity, botulinum type B neurotoxin activity, botulinum type D neurotoxin activity, botulinum type F neurotoxin activity and botulinum type G neurotoxin activity.

Suitably, the nucleic acid molecule is part of an expression vector.

Suitably, the nucleic acid molecule is within a genetically modified cell.

Suitably, the genetically modified cell is selected from the group consisting of a genetically modified SiMa neuroblastoma cell, LAN5 neuroblastoma cell, NG108 neuroblastoma cell, immortalised neuron and primary neuron.

Suitably, the kit further comprises reagents for the detection of luciferase activity.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The patent, scientific and technical literature referred to herein establish knowledge that was available to those skilled in the art at the time of filing. The entire disclosures of the issued patents, published and pending patent applications, and other publications that are cited herein are hereby incorporated by reference to the same extent as if each was specifically and individually indicated to be incorporated by reference. In the case of any inconsistencies, the present disclosure will prevail.

Various aspects of the invention are described in further detail below.

BRIEF DESCRIPTION OF THE DRAWINGS

Embodiments of the invention are further described hereinafter with reference to the accompanying drawings, in which:

FIG. 4 shows SiMa neuroblastoma cells engineered to carry NanoLuc-VAMP2 reporter exhibit cleavage after 48 hrs treatment with 10 nM botulinum neurotoxins type B and D. APEX2-VAMP reporter molecule is resistant to botulinum cleavage. The appearance of cleaved VAMP2 products is documented by immunoblotting using a total VAMP2 antibody. The evident faster migration of botulinum type D cleaved-product compared to botulinum type B cleaved-product is consistent with the cleavage of VAMP at Lys59 position instead of Gln76.

FIG. 5 shows immunoblot following titrations with BoNTs B and D (nM) revealing that SiMa cells are more sensitive to BoNT/B than BoNT/D. Detection using anti-VAMP2 antibody shows cleavage down to 1 nM for BoNT/B and 10 nM for BoNT/D. Detection using highly specific BoNT/B-cleaved VAMP2 and BoNT/D-cleaved VAMP2 antibodies shows cleavage down to 300 pM for BoNT/B and 10 nM for BoNT/D. Anti-BoNT/B cleaved VAMP2 and anti-BoNT/D cleaved VAMP2 antibodies were generated against the peptide ALQAGASQ (SEQ ID NO: 10) and the peptide KVLERDQK (SEQ ID NO: 11), respectively.

FIG. 6 shows comparison of sensitivity between immunoblotting and the NanoLuc ELISA assay with comparable $EC_{50}$s between the two techniques. However, the NanoLuc assay showed greater sensitivity with the ability to detect VAMP cleavage by BoNT/B above the baseline down to 30 pM (right panel). The NanoLuc ELISA assay involves capture of the botulinum cleaved NanoLuc-VAMP product on microplates carrying highly specific BoNT-cleaved VAMP2 antibodies with subsequent readings of light emission on microplate luminometer.

FIG. 7 shows immunoblotting and the NanoLuc assay can both be used to detect cleavage of VAMP2 by tetanus toxin, however, sensitivity in the SiMa neuroblastoma cells is lower than that seen with BoNT/B and BoNT/D.

FIG. 8 provides the amino acid sequence for human VAMP1 (SEQ ID NO:1). Amino acids 40 to 118 of human VAMP1 are underlined (SEQ ID NO:7).

FIG. 9 provides the amino acid sequence for human VAMP2 (SEQ ID NO:2). Amino acids 38 to 116 of human VAMP2 are underlined (SEQ ID NO:8).

FIG. 10 provides the amino acid sequence for human VAMP3 (SEQ ID NO:3). Amino acids 21 to 100 of human VAMP3 are underlined (SEQ ID NO:9).

FIG. 11 provides the amino acid sequence for NanoLuc (SEQ ID NO:4).

FIG. 12 provides the nucleic acid sequence for HA-APEX-VAMP2 construct (SEQ ID NO:5).

FIG. 13 provides the nucleic acid sequence for HA-NanoLuc-VAMP2 (SEQ ID NO:6).

FIG. 14 shows that Nanoluc-VAMP2 expressing cells can be used to differentiate potency of novel synthetic versions of BoNT/B designated here as I-IV. Immunoblots show different degrees of cleavage of Nanoluc-VAMP2 following 65 hrs applications of BoNT/B preparations I-IV in the indicated range (nM). Detection was using a cleaved VAMP2 antibody generated against the peptide ALQA-GASQ (SEQ ID NO: 10). Anti-SNAP25 antibody was used as a loading control.

FIG. 15 shows amino acids 40 to 118 of human VAMP1 (SEQ ID NO:7) (also referred to herein as the core amino acid sequence of VAMP1).

FIG. 16 shows amino acids 38 to 116 of human VAMP2 (SEQ ID NO:8) (also referred to herein as the core amino acid sequence of VAMP2).

FIG. 17 shows amino acids 21 to 100 of human VAMP3 (SEQ ID NO:9) (also referred to herein as the core amino acid sequence of VAMP3).

DETAILED DESCRIPTION

Figure 1:
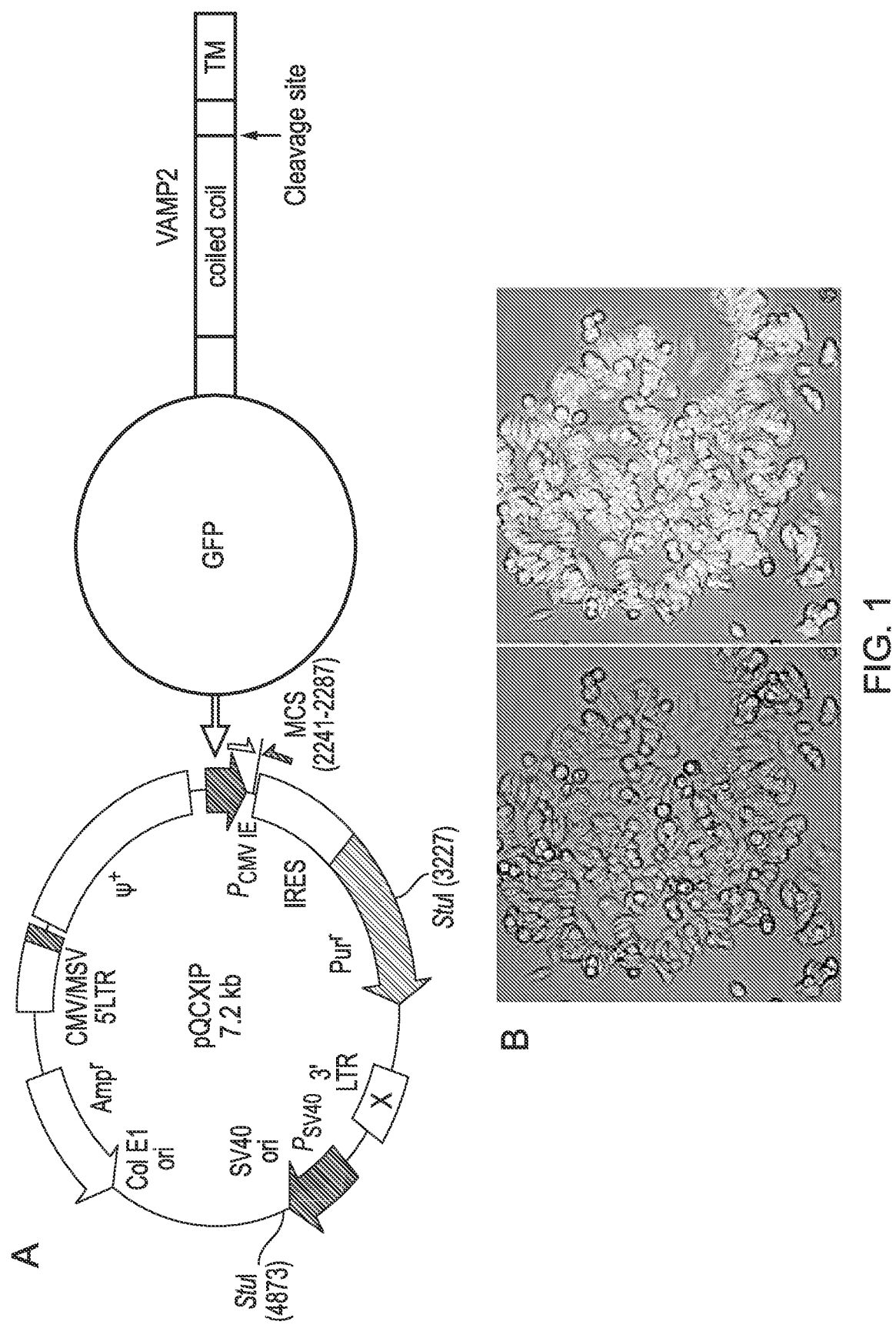
FIG. 1 shows, in panel A: Green Fluorescent Protein (GFP)-VAMP2 construct inserted in the indicated viral vector for infection of cells. Panel B: Neuroblastoma cells exhibit robust GFP-VAMP2 expression following puromycin selection. Bright-field and GFP fluorescent images are shown. Panel C: GFP-VAMP2 which localises to vesicular structures (top) can be released into the cytosol (lower left) upon expression of tetanus light chain fused to mCherry protein (lower right). Panel D: Stable cleaved GFP-VAMP2 product can be detected by conventional immunoblotting using GFP antibody.
Figure 1:
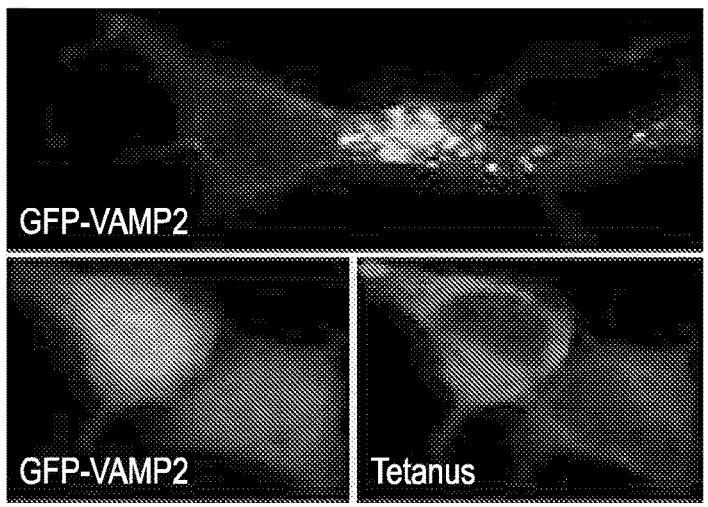
Figure 1:
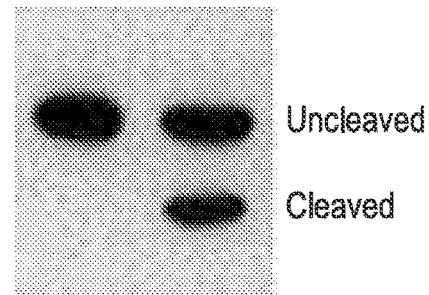

For several decades there has been a strong desire to replace cumbersome animal assays with an in vitro assay that enables sensitive evaluation of all key steps in tetanus and/or botulinum neurotoxin action. It was the dogma that continuous cell lines lacked the sensitivity necessary to develop an assay that could replace the mouse bioassay, but at the same time the use of primary neurons or embryonic cell-derived neurons pose their own challenges as they have to be freshly derived from animal tissue or they require complicated protocols and weeks/months to become fully differentiated. The first cell-based potency assay utilizing the SiMa neuroblastoma cell line measuring SNAP25-cleaving activity of therapeutic botulinum neurotoxin type A proved to be superior (EC50~1 U/well) to the mouse bioassay (11).

However, development of an equivalent assay for measuring VAMP-cleaving activity of tetanus and/or botulinum neurotoxins has proven challenging due to the rapid degradation of the VAMP cleavage products.

The inventors have now developed a novel reporter molecule that comprises an N-terminal polypeptide domain having luciferase activity and a C-terminal polypeptide domain having VAMP1, VAMP2 or VAMP3 activity. The reporter molecule is capable of being cleaved by tetanus neurotoxin, botulinum neurotoxin type B, botulinum neurotoxin type D, botulinum neurotoxin type F and/or botulinum neurotoxin type G (as well as modified versions thereof, including chimeras, that retain neurotoxin activity). Cleavage of the reporter molecule generates two cleavage products; a first fragment that comprises the N-terminal polypeptide domain having luciferase activity and a portion of the polypeptide domain having VAMP1, VAMP2 or VAMP3 activity; and a second fragment comprising the remaining portion of the polypeptide domain having VAMP1, VAMP2 or VAMP3 activity. Surprisingly, the N-terminal polypeptide domain having luciferase activity reduces or prevents degradation of the first fragment. Advantageously, the novel reporter molecule therefore provides a new mechanism for quantitative measurement of neurotoxin activity. Use of this novel reporter molecule (for example in a cell based assay using immortalised neuronal cell lines) is expected to accelerate botulinum and tetanus vaccine production as well as facilitate therapeutic botulinum product testing and diagnostic detection of botulism.

By way of a further example of the utility of the invention, it is shown that Nanoluc-VAMP2 expressing cells can be used to differentiate potency of novel synthetic versions of BoNT/B (see FIG. 14).

Polypeptides

A polypeptide is provided that comprises an N-terminal polypeptide domain having luciferase activity and a C-terminal polypeptide domain having VAMP1, VAMP2 or VAMP3 activity.

The terms "peptide", "protein" and "polypeptide" are used interchangeably herein.

The term polypeptide "domain" refers to a portion of a polypeptide sequence that can evolve, function and exist independently of the rest of the polypeptide chain. Typically, each domain within a polypeptide may form a compact three-dimensional structure and often can be independently stable and folded. An example of a polypeptide "domain" in the context of this disclosure is a domain having luciferase activity, a domain having VAMP1 activity, a domain having VAMP2 activity, or a domain having VAMP3 activity.

The N-terminus of a protein (also known as the amino-terminus, NH$_2$-terminus, N-terminal end or amine-terminus) is the start of a protein or polypeptide terminated by an amino acid with a free amine group (—NH$_2$). By convention, peptide sequences are written N-terminus to C-terminus (from left to right). The C-terminus (also known as the carboxyl-terminus, carboxy-terminus, C-terminal tail, C-terminal end, or COOH-terminus) is the end of an amino acid chain (protein or polypeptide), terminated by a free carboxyl group (—COOH).

As used herein, the terms "N-terminal" and "C-terminal" are used to describe the relative position of e.g. a domain within a polypeptide. Accordingly, a domain that is "N-terminal" is positioned closer (in relative terms) to the N-terminus than to the C-terminus of the polypeptide. Conversely, a domain that is "C-terminal" is positioned (in relative terms) closer to the C-terminus than to the N-terminus of the polypeptide. As used herein, the term "positioned" refers to the location of the e.g. domain within the linear amino acid sequence of the polypeptide.

The terms "N-terminal" and "C-terminal" can be used to describe the relative position of two or more domains within a polypeptide. In this context, a domain that is "N-terminal" is positioned closer (in relative terms) to the N-terminus of the polypeptide than a domain that is "C-terminal". Conversely, a domain that is "C-terminal" is positioned closer (in relative terms) to the C-terminus of the polypeptide than a domain that is "N-terminal".

A domain that is "N-terminal" may be, but does not have to be, at the N-terminus of the polypeptide (i.e. it may be, but does not have to be, at the start of the polypeptide terminated by an amino acid with a free amine group). In other words, the first amino acid of an N-terminal domain does not need to be (but may be) the first amino acid of the polypeptide. This means that there may be other amino acids, polypeptide domains (e.g. tags such as HA tags) etc between the N-terminus of the polypeptide and the start of the "N-terminal" domain (provided that the domain is positioned closer to the N-terminus than to the C-terminus of the polypeptide; or when used to describe the relative positions of two or more domains, provided that the domain is positioned closer to the N-terminus than a domain that is "C-terminal").

Likewise, a domain that is "C-terminal" may be, but does not have to be, at the C-terminus of the polypeptide (i.e. it may be, but does not have to be, at the end of the polypeptide terminated by any amino acid with a free carboxyl group). In other words, the last amino acid of a C-terminal domain does not need to be (but may be) the last amino acid of the polypeptide. This means that there may be other amino acids, polypeptide domains etc (e.g. tags) between the C-terminus of the polypeptide and the end of the "C-terminal" domain (provided that the domain is positioned closer to the C-terminus than to the N-terminus of the polypeptide; or when used to describe the relative positions of two or more domains, provided that the domain is positioned closer to the C-terminus than a domain that is "N-terminal").

Polypeptides comprising an N-terminal polypeptide domain (A) and a C-terminal polypeptide domain (B) are conventionally written as A-B i.e. N-terminal to C-terminal (left to right). By way of example, a polypeptide comprising an N-terminal enzyme luciferase (e.g. NanoLuc or "Nluc") domain and a C-terminal VAMP2 domain will be conventionally written as Nluc-VAMP2 (or NlucVAMP2).

By way of example, a polypeptide of the invention may comprise a HA tag N-terminal to the polypeptide domain having luciferase activity. Other suitable tags are well known in the art and may additionally or alternatively be used.

A linker may also be present between the domain having luciferase activity and the domain having VAMP1, VAMP2 or VAMP3 activity e.g. a proline glycine linker may be used. Other suitable linkers are well known in the art and may additionally or alternatively be used.

The polypeptides provided herein comprise an N-terminal polypeptide domain having an enzymatic luciferase activity.

A polypeptide domain having "luciferase activity" refers to a polypeptide domain that retains the functional activity of a luciferase enzyme i.e. it is capable of producing bioluminescence by oxidising a photon-emitting substrate, such as luciferin and furimazine [ACS Chem Biol. 2012 Nov. 16; 7(11): 1848-1857 'Engineered Luciferase Reporter from a Deep Sea Shrimp Utilizing a Novel Imidazopyrazinone Substrate' Hall et al]. As used herein, a polypeptide having "luciferase activity" includes any polypeptide from the luciferase class of oxidative enzymes that produce bioluminescence by oxidising luciferin or furimazine (i.e. it includes any functional luciferase). A person of skill in the art is readily aware of how to identify polypeptide domains with luciferase activity, using routine experiments known in the art. A suitable experiment for identifying functional luciferases is summarised in [Beyond D-luciferin: Expanding the Scope of Bioluminescence Imaging in vivo. Spencer T. Adams, Jr., Stephen C. Miller Curr Opin Chem Biol. 2014; 0: 112-120.]

In one embodiment, the polypeptide domain having luciferase activity comprises the amino acid sequence shown in SEQ ID NO: 4, or functional variants (or functional fragments) thereof. Such variants may be naturally occurring (e.g. allelic), synthetic, or synthetically improved functional variants of SEQ ID NO:4. The term "variant" also encompasses homologues.

Functional variants will typically contain only conservative substitutions of one or more amino acids of SEQ ID NO:4, or substitution, deletion or insertion of non-critical amino acids in non-critical regions of the protein. A functional variant of SEQ ID NO:4 may therefore be a conservative amino acid sequence variant of SEQ ID NO:4, wherein the variant has luciferase activity.

Non-functional variants are amino acid sequence variants of SEQ ID NO: 4 that do not have luciferase activity. Non-functional variants will typically contain a non-conservative substitution, a deletion, or insertion or premature truncation of the amino acid sequence of SEQ ID NO:4 or a substitution, insertion or deletion in critical amino acids or critical regions. Methods for identifying functional and non-functional variants (e.g. functional and non-functional allelic variants) are well known to a person of ordinary skill in the art.

A summary of the critical and non-critical amino acids in luciferase is provided in [Engineered luciferase reporter from a deep sea shrimp utilizing a novel imidazopyrazinone substrate. Hall M P, Unch J, Binkowski B F, Valley M P, Butler B L, Wood M G, Otto P, Zimmerman K, Vidugiris G, Machleidt T, Robers M B, Benink H A, Eggers C T, Slater M R, Meisenheimer P L, Klaubert D H, Fan F, Encell L P, Wood K V. ACS Chem Biol. 2012, 7(11):1848-57]. Accordingly, a person of skill in the art would readily be able to identify amino acids that may be substituted to provide functional variants (or functional fragments), such as conservative amino acid sequence variants, of SEQ ID NO:4. Homologues of SEQ ID NO:4 can also readily be identified using standard sequence alignment programmes by a person of ordinary skill in the art.

A polypeptide having luciferase activity may comprise an amino acid sequence having at least about 60%, 65%, 70%, 75%, 80%, 85%, 90%, 91%, 92%, 93%, 94%, 95%, 96%, 97%, 98%, 99% or 100% identity to the amino acid sequence of SEQ ID NO:4, or portions or fragments thereof. Suitably, percent identity can be calculated as the percentage of identity to the entire length of the reference sequence (e.g. SEQ ID NO:4), or portions or fragments thereof.

The amino acid sequence shown in SEQ ID NO:4 is that of the luciferase NanoLuc (sold by Promega). The terms "NanoLuc" and "NLuc" are used interchangeably herein. More details on the NanoLuc luciferase can be found in Hall et al., ACS chem Biol 2012, 7, μg 1848 to 1857.

Alternative examples of suitable luciferases include the firefly luciferase (FLuc; EC 1.13.12.7) from the firefly *Photinus pyralis*. Firefly luciferase is a euglobulin protein that catalyses the oxygenation of luciferin using ATP and molecular oxygen to yield oxyluciferin, a highly unstable, singlet-excited compound that emits light upon relaxation to its ground state. A variety of other organisms regulate their light production using different luciferases in a variety of light-emitting reactions (e.g the Jack-o-lantern mushroom *Omphalotus olearius*, several marine creatures such as the sea pansy (*Renilla reniformis*, with its luciferase Renilla-luciferin 2-monooxygenase; RLuc), and the luciferase of dinoflagellates). Other examples of luciferases include Modified Firefly luciferase (Ultra-GLo; derived from *Photuris pennsylvanica*), Click beetle luciferase (CBLuc; derived from *Pyrophorus plagiophthalamus*), Copepod crustacean luciferase (GLuc; derived from *Gaussia princeps*) and Ostracod crustacean luciferase (CLuc; derived from *Cypridina noctiluca*). A review of different luciferases commonly used in the art can be found in Thorne et al., Chem Biol. 2010 Jun. 25; 17(6); 646-657.

The polypeptides provided herein further comprise a C-terminal polypeptide domain having VAMP1, VAMP2 or VAMP3 activity.

As used herein, a polypeptide domain "having VAMP1, VAMP2 or VAMP3 activity" refers to a polypeptide domain that is capable of functioning as a VAMP1, VAMP2 or VAMP3 protein.

VAMPs cover a family of proteins which are characterised by a C-terminal integral membrane domain. The N-terminus (aa 1-90 or more depending on isoform and species) faces the cytosol and comprises a SNARE motif for the interaction with SNAP-25 and syntaxin. All VAMPs are engaged in membrane fusion processes. VAMPs interact by their N-terminal chain with syntaxin and SNAP-25 family members to form the fusion core or SNARE complex, as a prerequisite for exocytosis. The fundamental role of VAMP for vesicle fusion has been shown when analysing VAMP knockout animal models.

VAMP1 and VAMP2 are known as synaptobrevins and are expressed in brain, spinal cord and in peripheral neurons. They are constituents of the synaptic vesicles, where they participate in neurotransmitter release. VAMP3 (also known as cellubrevin) is ubiquitously expressed and participates in regulated and constitutive exocytosis as a constituent of secretory granules and secretory vesicles [Nature Reviews Molecular Cell Biology 2, 98-106 (February 2001) 'SNARE-mediated membrane fusion' Y. A. Chen & R. H. Scheller].

VAMP1, VAMP2 and VAMP3 are all known substrates for tetanus neurotoxin (TeNT), botulinum neurotoxin type B (BoNT/B), botulinum neurotoxin type D (BoNT/D), botulinum neurotoxin type F (BoNT/F), and botulinum neurotoxin type G (BoNT/G). The neurotoxins cleave the VAMP1, VAMP2 and VAMP3 substrates at conserved cleavage site sequences, as shown in table 1 below.

TABLE 1

| Toxin | Target SNAREs | Cleavage site sequence |
|---|---|---|
| BoNT/B | VAMP 1 | GASQ$^{78}$ FESS |
| TeNT | VAMP 2 | GASQ$^{76}$ FETS |
|  | VAMP 3 | GASQ$^{59}$ FETS |
| BoNT/D | VAMP 1 | RDQK$^{61}$ LSEL |
|  | VAMP 2 | RDQK$^{59}$ LSEL |
|  | VAMP 3 | RDQK$^{42}$ LSEL |
| BoNT/F | VAMP 1 | ERDQ$^{60}$ KLSE |
|  | VAMP 2 | ERDQ$^{58}$ KLSE |
|  | VAMP 3 | ERDQ$^{41}$ KLSE |
| BoNT/G | VAMP 1 | ESSA$^{83}$ AKLK |
|  | VAMP 2 | ETSA$^{81}$ AKLK |
|  | VAMP 3 | ETSA$^{64}$ AKLK |

A polypeptide domain having "VAMP1 activity" refers to a polypeptide domain that (i) retains the functional activity of VAMP1 i.e. it resides in vesicles and is capable of SNARE complex formation and (ii) is capable of being cleaved by at least one of, at least two of, at least three of, at least four of, or at least all of tetanus neurotoxin (TeNT), botulinum neurotoxin type B (BoNT/B), botulinum neurotoxin type D (BoNT/D), botulinum neurotoxin type F (BoNT/F), and botulinum neurotoxin type G (BoNT/G).

A person of skill in the art is readily aware of how to identify polypeptide domains with vesicle-associated VAMP1 activity, using routine experiments known in the art. A suitable experiment for identifying functional VAMP1 is summarised in [Identification of a minimal core of the synaptic SNARE complex sufficient for reversible assembly and disassembly. Fasshauer D, Eliason W K, Brünger A T, Jahn R. Biochemistry. 1998 Jul. 21; 37(29):10354-62.] and also in [Vesicular restriction of synaptobrevin suggests a role for calcium in membrane fusion. Hu K, Carroll J, Fedorovich S, Rickman C, Sukhodub A, Davletov B. Nature. 2002 Feb. 7; 415(6872):646-50].

A person of skill in the art is also readily aware of how to identify polypeptide domains that are capable of being cleaved by at least one of, at least two of, at least three of, at least four of, or at least all of tetanus neurotoxin (TeNT), botulinum neurotoxin type B (BoNT/B), botulinum neurotoxin type D (BoNT/D), botulinum neurotoxin type F (BoNT/F), and botulinum neurotoxin type G (BoNT/G), using routine experiments known in the art. A suitable experiment for identifying polypeptide domains that are capable of being cleaved as described is summarised in [Specificity of botulinum protease for human VAMP family proteins. Yamamoto H, et al. Microbiol Immunol, 2012 April PMID 22289120]. In addition, ample guidance of appropriate cleavage site sequences of VAMP1 are provided in table 1. The presence of one (or more) of these conserved cleavage site sequences in the polypeptide domain may also indicate that it is capable of being cleaved by tetanus neurotoxin (TeNT), botulinum neurotoxin type B (BoNT/B), botulinum neurotoxin type D (BoNT/D), botulinum neurotoxin type F (BoNT/F), and/or botulinum neurotoxin type G (BoNT/G), as appropriate.

In one embodiment, the polypeptide domain having VAMP1 activity comprises the amino acid sequence shown in SEQ ID NO: 1, or functional variants (or functional fragments) thereof. Such variants may be naturally occurring (e.g. allelic), synthetic, or synthetically improved functional variants of SEQ ID NO:1. The term "variant" also encompasses homologues.

In one embodiment, the polypeptide domain having VAMP1 activity comprises amino acids 40 to 118 of SEQ ID NO:1, or functional variants (or functional fragments) thereof. Such variants may be naturally occurring (e.g. allelic), synthetic, or synthetically improved functional variants of SEQ ID NO:1. The term "variant" also encompasses homologues.

Amino acids 40 to 118 of SEQ ID NO:1 represent the core VAMP1 amino acid sequence for BoNT interaction and cleavage (amino acids 40 to 118 are also referred to herein as SEQ ID NO:7, and are shown in FIG. 8 (underlined amino acids only) and in FIG. 15). The VAMP1 amino acid sequence, BoNT interaction and cleavage sites are well known in the art (see for example Yamamoto H, Ida T, Tsutsuki H, Mori M, Matsumoto T, Kohda T, Mukamoto M, Goshima N, Kozaki S, Ihara H. Microbiol Immunol. 2012 April; 56(4):245-53). Accordingly, other appropriate polypeptide domains having VAMP1 activity can also be readily determined by a person of skill in the art.

Functional variants will typically contain only conservative substitutions of one or more amino acids of SEQ ID NO:1, or substitution, deletion or insertion of non-critical amino acids in non-critical regions of the protein. A functional variant of SEQ ID NO:1 may therefore be a conservative amino acid sequence variant of SEQ ID NO:1, wherein the variant has VAMP1 activity.

Non-functional variants are amino acid sequence variants of SEQ ID NO:1 that do not have VAMP1 activity. Non-functional variants will typically contain a non-conservative substitution, a deletion, or insertion or premature truncation of the amino acid sequence of SEQ ID NO:1 or a substitution, insertion or deletion in critical amino acids or critical regions. Methods for identifying functional and non-functional variants (e.g. functional and non-functional allelic variants) are well known to a person of ordinary skill in the art.

A summary of the critical and non-critical amino acids in VAMP1 is provided in [Proc Natl Acad Sci USA. 1998 Dec. 22; 95(26):15781-6. Conserved structural features of the synaptic fusion complex: SNARE proteins reclassified as Q- and R-SNAREs. Fasshauer D, Sutton R B, Brunger A T, Jahn R]. Accordingly, a person of skill in the art would readily be able to identify amino acids that may be substituted to provide functional variants (or functional fragments), such as conservative amino acid sequence variants, of SEQ ID NO:1. Homologues of SEQ ID NO:1 can also readily be identified using standard sequence alignment programmes by a person of ordinary skill in the art.

A polypeptide having VAMP1 activity may comprise an amino acid sequence having at least about 60%, 65%, 70%, 75%, 80%, 85%, 90%, 91%, 92%, 93%, 94%, 95%, 96%, 97%, 98%, 99% or 100% identity to the amino acid sequence of SEQ ID NO:1, or portions or fragments thereof. Suitably, percent identity can be calculated as the percentage of identity to the entire length of the reference sequence (e.g. SEQ ID NO:1), or portions or fragments thereof.

The amino acid sequence shown in SEQ ID NO:1 is that of naturally occurring human VAMP1. More details on human VAMP1 can be found in [Specificity of botulinum protease for human VAMP family proteins. Yamamoto H, et al. Microbiol Immunol, 2012 April PMID 22289120]. A polypeptide domain having "VAMP2 activity" refers to a polypeptide domain that (i) retains the functional activity of VAMP2 i.e resides in vesicles and is capable of SNARE complex formation and (ii) is capable of being cleaved by at least one of, at least two of, at least three of, at least four of, or at least all of tetanus neurotoxin (TeNT), botulinum neurotoxin type B (BoNT/B), botulinum neurotoxin type D (BoNT/D), botulinum neurotoxin type F (BoNT/F), and botulinum neurotoxin type G (BoNT/G).

A person of skill in the art is readily aware of how to identify polypeptide domains with vesicle-associated VAMP2 activity, using routine experiments known in the art. A suitable experiment for identifying functional VAMP2 is summarised in [J Biol Chem. 1999 May 28; 274(22):15440-6. Mixed and non-cognate SNARE complexes. Characterization of assembly and biophysical properties. Fasshauer D, Antonin W, Margittai M, Pabst S, Jahn R.] and also in [Nature. 2002. Feb. 7; 415(6872):646-50. Vesicular restriction of synaptobrevin suggests a role for calcium in membrane fusion. Hu K, Carroll J, Fedorovich S, Rickman C, Sukhodub A, Daveltov B.]

A person of skill in the art is also readily aware of how to identify polypeptide domains that are capable of being cleaved by at least one of, at least two of, at least three of, at least four of, or at least all of tetanus neurotoxin (TeNT), botulinum neurotoxin type B (BoNT/B), botulinum neurotoxin type D (BoNT/D), botulinum neurotoxin type F (BoNT/F), and botulinum neurotoxin type G (BoNT/G), using routine experiments known in the art. A suitable experiment for identifying polypeptide domains that are capable of being cleaved as described is summarised in [Specificity of botulinum protease for human VAMP family proteins. Yamamoto H, et al. Microbiol Immunol, 2012 April PMID 22289120]. In addition, ample guidance of appropriate cleavage site sequences of VAMP2 are provided in table 1. The presence of one (or more) of these conserved cleavage site sequences in the polypeptide domain may also indicate that it is capable of being cleaved by tetanus neurotoxin (TeNT), botulinum neurotoxin type B (BoNT/B), botulinum neurotoxin type D (BoNT/D), botulinum neurotoxin type F (BoNT/F), and/or botulinum neurotoxin type G (BoNT/G), as appropriate.

In one embodiment, the polypeptide domain having VAMP2 activity comprises the amino acid sequence shown in SEQ ID NO:2, or functional variants (or functional fragments) thereof.

Such variants may be naturally occurring (e.g. allelic), synthetic, or synthetically improved functional variants of SEQ ID NO:2. The term "variant" also encompasses homologues.

In one embodiment, the polypeptide domain having VAMP2 activity comprises amino acids 38 to 116 of SEQ ID NO:2, or functional variants (or functional fragments) thereof. Such variants may be naturally occurring (e.g. allelic), synthetic, or synthetically improved functional variants of SEQ ID NO:2. The term "variant" also encompasses homologues.

Amino acids 38 to 116 of SEQ ID NO:2 represent the core VAMP2 amino acid sequence for BoNT interaction and cleavage (amino acids 38 to 116 are also referred to herein as SEQ ID NO:8, and are shown in FIG. 9 (underlined amino acids only) and in FIG. 16). The VAMP2 amino acid sequence, BoNT interaction and cleavage sites are well known in the art (see for example Yamamoto H, Ida T, Tsutsuki H, Mori M, Matsumoto T, Kohda T, Mukamoto M, Goshima N, Kozaki S, Ihara H. Microbiol Immunol. 2012 April; 56(4):245-53). Accordingly, other appropriate polypeptide domains having VAMP2 activity can also be readily determined by a person of skill in the art.

Functional variants will typically contain only conservative substitutions of one or more amino acids of SEQ ID NO:2, or substitution, deletion or insertion of non-critical amino acids in non-critical regions of the protein. A functional variant of SEQ ID NO:2 may therefore be a conservative amino acid sequence variant of SEQ ID NO:2, wherein the variant has VAMP2 activity.

Non-functional variants are amino acid sequence variants of SEQ ID NO:2 that do not have VAMP2 activity. Non-functional variants will typically contain a non-conservative substitution, a deletion, or insertion or premature truncation of the amino acid sequence of SEQ ID NO:2 or a substitution, insertion or deletion in critical amino acids or critical regions. Methods for identifying functional and non-functional variants (e.g. functional and non-functional allelic variants) are well known to a person of ordinary skill in the art.

A summary of the critical and non-critical amino acids in vesicle-associated VAMP2 is provided in [Proc Natl Acad Sci USA. 1998 Dec. 22; 95(26):15781-6. Conserved structural features of the synaptic fusion complex: SNARE proteins reclassified as Q- and R-SNAREs. Fasshauer D, Sutton R B, Brunger A T, Jahn R], and in [Proc Natl Acad Sci USA. 2006 May 30; 103(22):8378-83. Conformation of the synaptobrevin transmembrane domain. Bowen M, Brunger A T.]. Accordingly, a person of skill in the art would readily be able to identify amino acids that may be substituted to provide functional variants (or functional fragments), such as conservative amino acid sequence variants, of SEQ ID NO:2. Homologues of SEQ ID NO:2 can also readily be identified using standard sequence alignment programmes by a person of ordinary skill in the art.

A polypeptide having VAMP2 activity may comprise an amino acid sequence having at least about 60%, 65%, 70%, 75%, 80%, 85%, 90%, 91%, 92%, 93%, 94%, 95%, 96%, 97%, 98%, 99% or 100% identity to the amino acid sequence of SEQ ID NO:2, or portions or fragments thereof. Suitably, percent identity can be calculated as the percentage of identity to the entire length of the reference sequence (e.g. SEQ ID NO:2), or portions or fragments thereof.

The amino acid sequence shown in SEQ ID NO:2 is that of naturally occurring human VAMP2. More details on human VAMP2 can be found in [Substrate recognition of VAMP-2 by botulinum neurotoxin B and tetanus neurotoxin. Chen S, et al. J Biol Chem, 2008 Jul. 25. PMID 18511417].

A polypeptide domain having "VAMP3 activity" refers to a polypeptide domain that (i) retains the functional activity of VAMP3 i.e. it resides in vesicles and is capable of SNARE complex formation and (ii) is capable of being cleaved by at least one of, at least two of, at least three of, at least four of, or at least all of tetanus neurotoxin (TeNT), botulinum neurotoxin type B (BoNT/B), botulinum neurotoxin type D (BoNT/D), botulinum neurotoxin type F (BoNT/F), and botulinum neurotoxin type G (BoNT/G).

A person of skill in the art is readily aware of how to identify polypeptide domains with VAMP3 activity, using routine experiments known in the art. A suitable experiment for identifying functional VAMP3 is summarised in [J Biol Chem. 1999 May 28; 274(22):15440-6. Mixed and non-cognate SNARE complexes. Characterization of assembly and biophysical properties. Fasshauer D, Antonin W, Margittai M, Pabst S, Jahn R.].

A person of skill in the art is also readily aware of how to identify polypeptide domains that are capable of being cleaved by at least one of, at least two of, at least three of, at least four of, or at least all of tetanus neurotoxin (TeNT), botulinum neurotoxin type B (BoNT/B), botulinum neurotoxin type D (BoNT/D), botulinum neurotoxin type F (BoNT/F), and botulinum neurotoxin type G (BoNT/G), using routine experiments known in the art. A suitable experiment for identifying polypeptide domains that are capable of being cleaved as described is summarised in [Specificity of botulinum protease for human VAMP family proteins. Yamamoto H, et al. Microbiol Immunol, 2012 April PMID 22289120]. In addition, ample guidance of appropriate cleavage site sequences of VAMP3 are provided in table 1. The presence of one (or more) of these conserved cleavage site sequences in the polypeptide domain may also indicate that it is capable of being cleaved by tetanus neurotoxin (TeNT), botulinum neurotoxin type B (BoNT/B), botulinum neurotoxin type D (BoNT/D), botulinum neurotoxin type F (BoNT/F), and/or botulinum neurotoxin type G (BoNT/G), as appropriate.

In one embodiment, the polypeptide domain having VAMP3 activity comprises the amino acid sequence shown in SEQ ID NO:3, or functional variants (or functional fragments) thereof. Such variants may be naturally occurring (e.g. allelic), synthetic, or synthetically improved functional variants of SEQ ID NO:3. The term "variant" also encompasses homologues.

In one embodiment, the polypeptide domain having VAMP3 activity comprises amino acids 21 to 100 of SEQ ID NO:3, or functional variants (or functional fragments) thereof. Such variants may be naturally occurring (e.g. allelic), synthetic, or synthetically improved functional variants of SEQ ID NO:3. The term "variant" also encompasses homologues.

Amino acids 21 to 100 of SEQ ID NO:3 represent the core VAMP3 amino acid sequence for BoNT interaction and cleavage (amino acids 21 to 100 are also referred to herein as SEQ ID NO:9, and are shown in FIG. 10 (underlined amino acids only) and in FIG. 17). The VAMP3 amino acid sequence, BoNT interaction and cleavage sites are well known in the art (see for example Yamamoto H, Ida T, Tsutsuki H, Mori M, Matsumoto T, Kohda T, Mukamoto M, Goshima N, Kozaki S, Ihara H. Microbiol Immunol. 2012 April; 56(4):245-53). Accordingly, other appropriate polypeptide domains having VAMP3 activity can also be readily determined by a person of skill in the art.

Functional variants will typically contain only conservative substitutions of one or more amino acids of SEQ ID NO:3, or substitution, deletion or insertion of non-critical amino acids in non-critical regions of the protein. A functional variant of SEQ ID NO:3 may therefore be a conservative amino acid sequence variant of SEQ ID NO:3, wherein the variant has VAMP3 activity.

Non-functional variants are amino acid sequence variants of SEQ ID NO:3 that do not have VAMP3 activity. Non-functional variants will typically contain a non-conservative substitution, a deletion, or insertion or premature truncation of the amino acid sequence of SEQ ID NO:3 or a substitution, insertion or deletion in critical amino acids or critical regions. Methods for identifying functional and non-functional variants (e.g. functional and non-functional allelic variants) are well known to a person of ordinary skill in the art.

A summary of the critical and non-critical amino acids in VAMP3 is provided in [Proc Natl Acad Sci USA. 1998 Dec. 22; 95(26):15781-6. Conserved structural features of the synaptic fusion complex: SNARE proteins reclassified as Q- and R-SNAREs. Fasshauer D, Sutton R B, Brunger A T, Jahn R]. Accordingly, a person of skill in the art would readily be able to identify amino acids that may be substituted to provide functional variants (or functional fragments), such as conservative amino acid sequence variants, of SEQ ID NO:3. Homologues of SEQ ID NO:3 can also readily be identified using standard sequence alignment programmes by a person of ordinary skill in the art.

A polypeptide having VAMP3 activity may comprise an amino acid sequence having at least about 60%, 65%, 70%, 75%, 80%, 85%, 90%, 91%, 92%, 93%, 94%, 95%, 96%, 97%, 98%, 99% or 100% identity to the amino acid sequence of SEQ ID NO:3, or portions or fragments thereof. Suitably, percent identity can be calculated as the percentage of identity to the entire length of the reference sequence (e.g. SEQ ID NO:3), or portions or fragments thereof.

The amino acid sequence shown in SEQ ID NO:3 is that of naturally occurring human VAMP3. More details on human VAMP3 can be found in [Nature Reviews Molecular Cell Biology 2, 98-106 (February 2001) SNARE-mediated membrane fusion' Y. A. Chen & R. H. Scheller].

A "non-essential" or "non-critical" amino acid residue is a residue that can be altered from the wild-type sequence of (e.g., the sequence of SEQ ID NO:1 to 4) without abolishing or, more preferably, without substantially altering a biological activity, whereas an "essential" amino acid residue results in such a change. For example, amino acid residues that are conserved among the polypeptides of the present invention are predicted to be particularly non-amenable to alteration, except that amino acid residues in transmembrane domains can generally be replaced by other residues having approximately equivalent hydrophobicity without significantly altering activity.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in protein is preferably replaced with another amino acid residue from the same side chain family. Alternatively, in another embodiment, mutations can be introduced randomly along all or part of coding sequences, such as by saturation mutagenesis, and the resultant mutants can be screened for biological activity to identify mutants that retain activity. Following mutagenesis of SEQ ID NO:1 to 4, the encoded proteins can be expressed recombinantly and the biological activity of the protein can be determined.

As used herein, a "biologically active portion" of protein or a protein portion with "biological activity" includes fragment of protein that participate in an interaction between molecules and non-molecules. Biologically active portions of protein include peptides comprising amino acid sequences sufficiently homologous to or derived from the amino acid sequences of the protein, e.g., the amino acid sequences shown in SEQ ID NO: 1 to 4, which include fewer amino acids than the full length protein, and exhibit at least one activity of the encoded protein. Typically, biologically active portions comprise a domain or motif with at least one activity of the protein, e.g., the biologically active portion may retain one of the following activities (as appropriate); luciferase, VAMP1, VAMP2 or VAMP3 activity.

A biologically active portion of protein can be a polypeptide that is, for example, 50, 100, 150, 200, 250, 300, 350, 400, 450, 500 or more amino acids in length of SEQ ID NO:1 to 4. Biologically active portions of protein can be used as targets for developing agents that modulate mediated activities, e.g., biological activities described herein.

Calculations of sequence homology or identity (the terms are used interchangeably herein) between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

Alternatively, the percent identity between two amino acid or nucleotide sequences can be determined using the algorithm of Meyers et al. (1989) CAB/OS 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-410). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, gapped BLAST can be utilized as described in Altschul et al. (1997, *Nucl. Acids Res.* 25:3389-3402). When using BLAST and gapped BLAST programs, the default parameters of the respective programs (e.g., XBLAST and NBLAST) can be used.

The polypeptides described herein can have amino acid sequences sufficiently or substantially identical to the amino acid sequences of SEQ ID NO:1 to 4. The terms "sufficiently identical" or "substantially identical" are used herein to refer to a first amino acid or nucleotide sequence that contains a sufficient or minimum number of identical or equivalent (e.g. with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as sufficiently or substantially identical.

Nucleic Acid Molecules

Nucleic acid molecules encoding a polypeptide described herein are also provided.

The nucleic acid molecule encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R et al (Science (1988) 239, pp 487-491).

The nucleotide sequence may be a mix of genomic and exogenous origin in accordance with standard techniques. For example, the nucleotide sequence may be generated using gene editing techniques such as CRISPR/Cas9, wherein a nucleic acid sequence encoding a domain having luciferase activity is introduced upstream of a native nucleic acid sequence encoding a domain having VAMP1, VAMP2 or VAMP3 activity.

The term "nucleic acid molecule" or "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand. The term "nucleotide sequence" in relation to the present invention includes genomic DNA, cDNA, synthetic DNA, and RNA (e.g. mRNA) and analogs of the DNA or RNA generated, e.g., by the use of nucleotide analogs.

The nucleic acid molecule can be single-stranded or double-stranded, but preferably is double-stranded DNA, more preferably cDNA for the coding sequence. In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence" or "non-naturally occurring sequence". In this regard, the term "native nucleotide sequence" or "naturally occurring sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" or "naturally occurring polypeptide" means an entire polypeptide that is in its native environment and when it has been expressed by its native nucleotide sequence. Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

As used herein, the term "recombinant" refers to a biomolecule, for example a gene or a protein that (1) has been removed from its naturally occurring (native) environment, (2) is not associated with all or a portion of a nucleic acid molecule or protein as it is found in nature, (3) is operatively linked to a polynucleotide or polypeptide which it is not linked to in nature, or (4) does not occur in nature.

By way of example, a polypeptide comprising an N-terminal polypeptide domain having luciferase activity and a C-terminal polypeptide domain having VAMP1, VAMP2 or VAMP3 activity is considered a recombinant biomolecule (as are all of the specific embodiments of polypeptides provided herein). Likewise, the nucleic acid molecules encoding the polypeptides provided herein are also "recombinant".

Hybridisation

The present invention also encompasses the use of sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

Hybridisation conditions are based on the melting temperature (Tm) of the nucleotide binding complex, as taught in Berger and Immel (1987, Guide to Molecular Cloning Techniques, Methods in Enzymology, Vol. 152, Academic Press, San Diego, Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses the use of sequences that are that are capable of hybridising under intermediate stringency conditions (e.g. 50° C. and 0.2× SSC) or high stringency conditions (e.g. 65° C. and 0.1×SSC {1×SSC-0.15 M NaCl, 0.015 M Na-citrate pH 7.0}) to a nucleotide sequence (or complementary sequence thereof) defined herein.

Expression Vector

As used herein, the term "vector" or "construct" refers to a nucleic acid molecule capable of transporting another nucleic acid to which it has been operably linked. The terms "vector" and "construct" are used interchangeably herein.

The vector can be capable of autonomous replication or it can integrate into a host DNA. The vector may include restriction enzyme sites for insertion of recombinant DNA and may include one or more selectable markers. The vector can be a nucleic acid molecule in the form of a plasmid, a bacteriophage or a cosmid.

Preferably the vector is suitable for expression in a cell (i.e. the vector is an "expression vector"). Preferably, the expression vector is suitable for expression in a neuronal cell or neuronal cell line. Most preferably, the vector is suitable for expression in neuroblastoma cells lines (e.g. SiMa neuroblastoma cells, LAN5 neuroblastoma cells, or NG108 neuroblastoma cells), immortalized neurons, primary neurons or genetically-modified organisms.

Preferably the (expression) vector is capable of propagation in a host cell and is stably transmitted to future generations.

"Operably linked" as used herein, refers to a single or a combination of the below-described control elements together with a coding sequence in a functional relationship with one another, for example, in a linked relationship so as to direct expression of the coding sequence.

"Regulatory sequences" as used herein, refers to, DNA or RNA elements that are capable of controlling gene expression. Examples of expression control sequences include promoters, enhancers, silencers, Shine Dalgarno sequences, TATA-boxes, internal ribosomal entry sites (IRES), attachment sites for transcription factors, transcriptional terminators, polyadenylation sites, RNA transporting signals or sequences important for UV-light mediated gene response. Preferably the vector includes one or more regulatory sequences operatively linked to the nucleic acid sequence to be expressed. Regulatory sequences include those which direct constitutive expression, as well as tissue-specific regulatory and/or inducible sequences.

"Promoter", as used herein, refers to the nucleotide sequences in DNA or RNA to which RNA polymerase binds to begin transcription. The promoter may be inducible or constitutively expressed. Alternatively, the promoter is under the control of a repressor or stimulatory protein. Preferably the promoter is selected from SV40, CMV, Actin, EF1 alpha, UB, RCV, PGK, CAG, MMLV-LTR or CMV-LTR hybrid promoters.

"Transcriptional terminator" as used herein, refers to a DNA element, which terminates the function of RNA polymerases responsible for transcribing DNA into RNA. Preferred transcriptional terminators are characterized by a run of T residues preceded by a GC rich dyad symmetrical region.

"Translational control element", as used herein, refers to DNA or RNA elements that control the translation of mRNA. Preferred translational control elements are ribosome binding sites. Preferably, the translational control element is from a homologous system as the promoter, for example a promoter and its associated ribozyme binding site. Preferred ribosome binding sites are T7 or T3 ribosome binding sites.

"Restriction enzyme recognition site" as used herein, refers to a motif on the DNA recognized by a restriction enzyme.

"Selectable marker" as used herein, refers to proteins that, when expressed in a host cell, confer a phenotype onto the cell which allows a selection of the cell expressing said selectable marker gene. Generally this may be a protein that confers resistance to an antibiotic such as ampicillin, kanamycin, chloramphenicol, tetracyclin, hygromycin, neomycin or methotrexate. Further examples of antibiotics are Penicillins; Ampicillin HCl, Ampicillin Na, Amoxycillin Na, Carbenicillin sodium, Penicillin G, Cephalosporins, Cefotaxim Na, Cefalexin HCl, Vancomycin, Cycloserine. Other examples include Bacteriostatic Inhibitors such as: Chloramphenicol, Erythromycin, Lincomycin, Tetracyclin, Spectinomycin sulfate, Clindamycin HCl, Chlortetracycline HCl.

The design of the expression vector depends on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g. a polypeptide comprising an N-terminal polypeptide domain having luciferase activity and a C-terminal domain having VAMP1, VAMP2 or VAMP3 activity).

Preferably the vector comprises those genetic elements which are necessary for expression of the polypeptides described herein by a host cell. The elements required for transcription and translation in the host cell include a promoter, a coding region for the protein(s) of interest, and a transcriptional terminator.

Expression vectors of the invention can be standard expression vectors such as pCDNA3, pIRES-NEO or retroviral vectors such as pQCXIP, pQCXIN, pQCXIG, pLXIN, pBMN, pBABE-hygro, and pBABE-puro.

The terms "expression vector", "expression construct", "construct" and "vector" are used interchangeably herein.

Preferably, the expression vector is a high-copy-number expression vector; alternatively, the expression vector is a low-copy-number expression vector.

Preparation of Expression Vectors

A person of skill in the art will be aware of the molecular techniques available for the preparation of expression vectors.

The nucleic acid molecule for incorporation into the expression vector of the invention, as described above, can be prepared by synthesizing nucleic acid molecules using mutually priming oligonucleotides and the nucleic acid sequences described herein.

A number of molecular techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites are used to operably link the nucleic acid molecule to the expression vector. In one embodiment, the nucleic acid molecule is generated by restriction endonuclease digestion. Preferably, the nucleic acid molecule is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a nucleic acid molecule carrying polymeric linker sequences at its ends. These nucleic acid molecules are then cleaved with the appropriate restriction enzyme and ligated to an expression vector that has been cleaved with an enzyme that produces termini compatible with those of the nucleic acid molecule.

Alternatively, a vector comprising ligation-independent cloning (LIC) sites can be employed. The required PCR amplified nucleic acid molecule can then be cloned into the LIC vector without restriction digest or ligation (Aslanidis and de Jong, *Nucl. Acid. Res.* 18, 6069-6074, (1990), Haun, et al, *Biotechniques* 13, 515-518 (1992).

In order to isolate and/or modify the nucleic acid molecule of interest for insertion into the chosen plasmid, it is preferable to use PCR. Appropriate primers for use in PCR preparation of the sequence can be designed to isolate the required coding region of the nucleic acid molecule, add restriction endonuclease or LIC sites, place the coding region in the desired reading frame.

In a preferred embodiment a nucleic acid molecule for incorporation into an expression vector of the invention, is prepared by the use of the polymerase chain reaction as disclosed by Saiki et al (1988) *Science* 239, 487-491, using appropriate oligonucleotide primers. The coding region is amplified, whilst the primers themselves become incorporated into the amplified sequence product. In a preferred embodiment the amplification primers contain restriction endonuclease recognition sites which allow the amplified sequence product to be cloned into an appropriate vector.

Preferably, the nucleic acid molecule is obtained by PCR and introduced into an expression vector using restriction endonuclease digestion and ligation, a technique which is well known in the art. More preferably, the nucleic acid molecule of is introduced into an expression vector such as pCDNA3, pIRES-NEO or a retroviral vector such as pQCXIP, pQCXIN, pQCXIG, pLXIN, pBMN, pBABE-hygro, or pBABE-puro.

The expression vectors of the invention can contain a single copy of the nucleic acid molecule described previously, or multiple copies of the nucleic acid molecule described previously.

The nucleic acid molecules and/or expression vectors described herein may be present within any appropriate host cell (thereby generating a genetically modified cell).

Host Cells

The term "host cell" in relation to the present invention includes any cell that comprises a nucleotide sequence according to the present invention or a nucleotide sequence encoding for a polypeptide having the specific properties as defined herein. Preferably the nucleotide sequence is incorporated in the genome of the cell.

The terms "host cell", "genetically modified cell" and "recombinant host cell" are used interchangeably. These terms do not cover native nucleotide coding sequences in their natural environment when they are under the control of their native promoter which is also in its natural environment, but refer to a genetically altered (e.g. transformed or transfected) cell. The terms refer to the particular subject cell and also to the progeny or potential progeny of such a cell. Because certain modifications may occur in succeeding generations due to either mutation or environmental influences, such progeny may not, in fact, be identical to the parent cell, but are still included within the scope of the term as used herein.

The genetically modified cell may be a eukaryotic cell or a prokaryotic cell. Preferably, the genetically modified cell is a clostridia sensitive cell (e.g. a cell (e.g. a clone/cell line) to which clostridia neurotoxins can bind and translocate across the cell membrane). Examples of such cells are well known and a skilled person would be able to readily identify such cells, for example by testing whether or not tetanus neurotoxin and/or botulinum neurotoxin (e.g. BoNT type B, BoNT type D, BoNT type F and/or BoNT type G) can bind and translocate across the cell membrane. Routine experiments for testing this are well known, including some of the experiments described in the examples section below. Suitable cells include cells of a neuroblastoma cell line (e.g. SiMa neuroblastoma cells, LAN5 neuroblastoma cells, NG108 neuroblastoma cells), immortalized neurons, primary neurons or genetically-modified organisms.

The host cell genome may be altered to generate the nucleic acid sequence of the invention, using any suitable means e.g. gene editing techniques that introduce a nucleic acid sequence encoding a protein domain having luciferase activity upstream of a native (endogenous) nucleic acid sequence encoding a protein domain having VAMP1, VAMP2 or VAMP3 activity. Alternatively or additionally, host cells may be transformed, infected or transfected with an expression vector of the invention using standard techniques known in the art.

Host Cell Transformation

A host cell transformed, infected or transfected with an expression vector of the invention, comprising a nucleic acid molecule as described previously, can be used to produce (i.e. express) a polypeptide of as provided herein.

The expression vector of the present invention can be introduced into cells by conventional transformation, transfection or transduction techniques. "Transformation", "transfection" and "transduction" refer to techniques for introducing foreign nucleic acids into a cell. The specific method used typically depends on both the type of vector and the cell. Said techniques include, but are not limited to calcium phosphate or calcium chloride co-precipitation, DEAE-dextran-mediated transfection, lipofection, chemoporation or electroporation.

Techniques known in the art for the transformation, transfection or transduction of cells are disclosed in for example, Sambrook et al (1989) Molecular Cloning, A Laboratory Manual, Cold Spring Harbor Laboratory, Cold Spring Harbor, N.Y; Ausubel et al (1987) Current Protocols in Molecular Biology, John Wiley and Sons, Inc., NY; Cohen et al (1972) Proc. Natl. Acad. Sci. USA 69, 2110; Luchansky et al (1988) Mol. Microbiol. 2, 637-646.

Successfully transformed, transfected or transduced cells (or genetically modified cells), that is, those cells containing the expression vector or nucleic acid molecule of the present invention, can be identified by techniques that are well known in the art. For example, cells transfected with the expression vector of the present invention can be cultured to produce proteins having luciferase activity and VAMP1, VAMP2 or VAMP3 activity. Cells can be examined for the presence of the expression vector DNA by techniques well known in the art. Alternatively, the presence of the polypeptide, or portion and fragments thereof can be detected using antibodies which hybridize thereto.

In a preferred embodiment the invention comprises a culture of transformed cells. Preferably the culture is clonally homogeneous.

The cell can contain a single copy of the expression vector described previously, or alternatively, multiple copies of the expression vector.

Uses and Methods

The inventors have surprisingly identified novel reporter molecules that can be used to detect neurotoxin activity (specifically tetanus, botulinum type B, botulinum type D, botulinum type F and/or botulinum type G neurotoxin activity). Upon cleavage of the reporter molecule by a specified neurotoxin, two cleavage fragments are generated; a first fragment comprising a N-terminal polypeptide domain having luciferase activity and a portion of a C-terminal polypeptide domain having VAMP1, VAMP2 or VAMP3 activity; and a second fragment comprising the remaining portion of the C-terminal polypeptide having VAMP1, VAMP2 or VAMP3 activity. Advantageously, the first fragment is sufficiently stable to enable detection of neurotoxin activity (i.e. detection of reporter molecule cleavage).

The polypeptide, nucleic acid molecule, expression vector or genetically modified cell of the invention may therefore be used for the detection of neurotoxin activity, wherein the neurotoxin activity is selected from the group consisting of tetanus neurotoxin activity, botulinum type B neurotoxin activity, botulinum type D neurotoxin activity, botulinum type F neurotoxin activity and botulinum type G neurotoxin activity.

As used herein "neurotoxin activity" refers to the ability of any one of naturally occurring tetanus, botulinum type B, botulinum type D, botulinum type F and botulinum type G neurotoxin(s) to cleave their substrate (in this case the polypeptide domain having VAMP1, VAMP or VAMP3 activity). Naturally occurring neurotoxins and their respective neurotoxin activity are well known in the art, and are described elsewhere in more detail (see Table 1 and also for example Botulinum Neurotoxins. Editors: Rummel, Andreas, Binz, Thomas (Eds.) Springer, Current Topics in Microbiology and Immunology, 2013).

For example, "tetanus neurotoxin activity" refers to the cleavage of VAMP1 (or a polypeptide domain having VAMP1 activity) at the cleavage site GASQ$^{78}$FESS (SEQ ID NO: 12), cleavage of VAMP2 (or a polypeptide domain having VAMP2 activity) at the cleavage site GASQ$^{76}$FETS (SEQ ID NO: 13), and/or cleavage of VAMP3 (or a polypeptide domain having VAMP3 activity) at the cleavage site GASQ$^{59}$FETS (SEQ ID NO: 14).

For example, "botulinum type B neurotoxin activity" refers to the cleavage of VAMP1 (or a polypeptide domain having VAMP1 activity) at the cleavage site GASQ$^{78}$FESS (SEQ ID NO: 12), cleavage of VAMP2 (or a polypeptide domain having VAMP2 activity) at the cleavage site GASQ$^{76}$FETS (SEQ ID NO: 13), and/or cleavage of VAMP3 (or a polypeptide domain having VAMP3 activity) at the cleavage site GASQ$^{59}$FETS (SEQ ID NO: 14).

For example, "botulinum type D neurotoxin activity" refers to the cleavage of VAMP1 (or a polypeptide domain having VAMP1 activity) at the cleavage site RDQK$^{61}$LSEL (SEQ ID NO: 15), cleavage of VAMP2 (or a polypeptide domain having VAMP2 activity) at the cleavage site RDQK$^{59}$LSEL (SEQ ID NO: 16), and/or cleavage of VAMP3 (or a polypeptide domain having VAMP3 activity) at the cleavage site RDQK$^{42}$LSEL (SEQ ID NO: 17).

For example, "botulinum type F neurotoxin activity" refers to the cleavage of VAMP1 (or a polypeptide domain having VAMP1 activity) at the cleavage site ERDQ$^{60}$KLSE (SEQ ID NO: 18), cleavage of VAMP2 (or a polypeptide domain having VAMP2 activity) at the cleavage site ERDQ$^{58}$KLSE (SEQ ID NO: 19), and/or cleavage of VAMP3 (or a polypeptide domain having VAMP3 activity) at the cleavage site ERDQ$^{41}$KLSE (SEQ ID NO: 20).

For example, "botulinum type G neurotoxin activity" refers to the cleavage of VAMP1 (or a polypeptide domain having VAMP1 activity) at the cleavage site ESSA$^{83}$AKLK (SEQ ID NO: 21), cleavage of VAMP2 (or a polypeptide domain having VAMP2 activity) at the cleavage site ETSA$^{81}$AKLK (SEQ ID NO: 22), and/or cleavage of VAMP3 (or a polypeptide domain having VAMP3 activity) at the cleavage site ETSA$^{64}$AKLK (SEQ ID NO: 23).

Modified versions (e.g. artificially modified, recombinants, chimeras, toxoids etc) of the tetanus, botulinum type B, botulinum type D, botulinum type F and/or botulinum type G neurotoxin(s) may retain "neurotoxin activity" (i.e. their ability to cleave VAMP1, VAMP2 and/or VAMP3 in the manner shown in Table 1). The invention can therefore be used to detect whether such modified neurotoxins retain "neurotoxin activity". Such uses and methods are encompassed by the invention.

The diversity of botulinum neurotoxins is summarized in, for example, [Research in Microbiology, Volume 166, Issue 4, May 2015, Pages 303-317, Genomes, neurotoxins and biology of Clostridium botulinum Group I and Group II, Andrew T. Carter, Michael W. Peck].

The invention can thus be used to detect the neurotoxin activity (and/or presence) of the naturally occurring forms of these neurotoxins, as well as the neurotoxin activity of chimeras, or artificially modified forms thereof. Advantageously, the invention therefore provides a means for testing modified forms of these neurotoxins for increased or decreased neurotoxin activity.

Any suitable means for detecting neurotoxin activity may be used. Several standard techniques may be used to detect cleavage of the polypeptides described herein. Exemplary techniques include, but are not limited to immunoblotting (also known as western blotting), sandwich ELISA assays or live cell imaging. Such methods or routine in the field and the details of how to perform each is well known (see for example [Specificity of botulinum protease for human VAMP family proteins. Yamamoto H, et al. Microbiol Immunol, 2012 April PMID 22289120; Substrate recognition of VAMP-2 by botulinum neurotoxin B and tetanus neurotoxin. Chen S, et al. J Biol Chem, 2008 Jul. 25. PMID 18511417]).

Detection of neurotoxin activity may be performed in vitro, in the absence of a genetically modified cell. For example, a polypeptide of the invention may be contacted with a neurotoxin (or test sample as described below) and the presence of cleaved product may be determined (e.g. by ELISA or western blotting). The development of such detection methods is well within the routine capabilities of a person of skill in the art.

Detection of neurotoxin activity may alternatively be performed using a genetically modified cell, as described elsewhere herein. Advantageously, a genetically modified cell provides a means for testing all three stages of neurotoxin action, namely binding to the cell surface, delivery of the neurotoxin peptidase into the cell cytosol and neurotoxin-induced cleavage of its substrate (in this case a polypeptide of the invention). The presence of cleaved product may be determined (e.g. by ELISA or western blotting of a cell lysate). Live cell imaging can also be used to detect neurotoxin activity as the "first fragment" generated by neurotoxin cleavage of the polypeptide (i.e the fragment comprising the N-terminal polypeptide domain having luciferase activity and a portion the C-terminal domain having VAMP1, VAMP2 or VAMP3 activity) will no longer be vesicle bound, but will be present in the cell cytosol. The development of such detection methods is well within the routine capabilities of a person of skill in the art.

Luciferase activity of the cleaved polypeptide can also be used in the detection of neurotoxin-induced cleavage. Standard techniques involving luciferase detection as well known in the art and the development of such methods is well within the routine capabilities of a person of skill in the art. A review of luciferase detection methods can be found in [Application of enzyme bioluminescence for medical diagnostics. Frank L A, Krasitskaya V V. Adv Biochem Eng Biotechnol. 2014; 144:175-97; Current advanced bioluminescence technology in drug discovery. Hoshino H. Expert Opin Drug Discov. 2009 April; 4(4):373-89].

Antibodies specific to the cleaved ends of the polypeptide may also be used in the detection of neurotoxin-induced cleavage. One advantage of using antibodies that are specific to the cleaved ends of the polypeptide is that they can be used to determine which specific neurotoxin (e.g. tetanus/BoNT type B, BoNT type D, BoNT type F or BoNT type G—see table 1) is responsible for cleavage of the polypeptide (and thus which neurotoxin is present within the e.g. test sample as described below).

By way of example, antibodies specific to BoNT/B cleaved VAMP2 or BoNT/D cleaved VAMP2 can be generated (antibodies were raised against the peptide ALQAGASQ (SEQ ID NO: 10) and the peptide KVLERDQK (SEQ ID NO: 11) respectively see FIG. 5 and the corresponding figure legend).

The invention may be used to detect neurotoxin activity in a test sample.

As used herein, "a test sample" may be any sample (with a known, unknown or partially known composition) that is to be tested for the presence of neurotoxin activity, wherein the neurotoxin activity is selected from the group consisting of: tetanus neurotoxin activity, botulinum type B neurotoxin activity, botulinum type D neurotoxin activity, botulinum type F neurotoxin activity and botulinum type G neurotoxin activity, or any combination thereof.

A "test sample" may comprise drug product (e.g. a vaccine for administration to a subject, such as a toxoid, where a toxoid a chemically modified toxin from a pathogenic microorganism (e.g. tetanus or botulinum), which is no longer toxic but is still antigenic and can be used as a vaccine). In such cases, the invention may be used to detect (unwanted) residual neurotoxin activity.

As used herein, a "subject" refers to a human or animal (e.g. to be vaccinated). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate, e.g., a human. A subject can be male or female. A subject can be a fully developed subject (e.g., an adult) or a subject undergoing the developmental process (e.g., a child, infant or fetus).

Preferably, the subject is a mammal. The mammal can be a human, non-human primate, mouse, rat, dog, cat, horse, or cow, but are not limited to these examples.

A suitable test sample may also comprise a food sample, a clinical sample or an environmental sample (wherein the food sample, clinical sample or environmental sample may have been contaminated with clostridium, and/or may contain a neurotoxin), or any combination thereof. In such cases, the invention may be used to detect the presence of contamination.

Suitable test samples also comprise a tetanus neurotoxin, botulinum neurotoxin type B, botulinum neurotoxin type D, botulinum neurotoxin type F and/or botulinum neurotoxin type G (for example a test sample from a known batch of neurotoxin, optionally manufactured for therapeutic or non-therapeutic use), or any combination thereof. In such cases, the invention may be used to detect or determine the potency of the neurotoxin. For the avoidance of doubt, the neurotoxins in the test sample may be naturally occurring neurotoxins, or may be modified (e.g. artificially modified, including chimeras) versions thereof.

In a preferred method, neurotoxin activity is detected (or determined) using a genetically modified cell of the invention, wherein the cell is cultured under conditions that allow for expression of a polypeptide comprising an N-terminal polypeptide domain having luciferase activity and a C-terminal polypeptide having VAMP1, VAMP2 or VAMP3 activity. In this example, the genetically modified cell may be contacted with a neurotoxin (or test sample) and the presence of cleaved product may be determined (e.g. by ELISA, western blotting or live cell imaging). The development of such methods is also well within the routine capabilities of a person of skill in the art.

Accordingly, a method of detecting neurotoxin activity in a test sample is provided, the method comprising:

(a) culturing a genetically modified cell according to the invention under conditions that allow for expression of a polypeptide comprising an N-terminal polypeptide domain having luciferase activity and a C-terminal polypeptide having VAMP1, VAMP2 or VAMP3 activity;

(b) culturing the cell of (a) in the presence of the test sample under conditions that allow for neurotoxin-induced cleavage of the polypeptide comprising an N-terminal polypeptide domain having luciferase activity and a C-terminal polypeptide having VAMP1, VAMP2 or VAMP3 activity; and (c) determining the level of neurotoxin-induced cleavage of the polypeptide, wherein detection of neurotoxin-induced cleavage of the polypeptide is indicative of neurotoxin activity; wherein the neurotoxin activity is selected from the group consisting of: tetanus neurotoxin activity, botulinum type B neurotoxin activity, botulinum type D neurotoxin activity, botulinum type F neurotoxin activity and botulinum type G neurotoxin activity, or any combination thereof.

The culture conditions in step (a) are such that they allow for expression of a polypeptide comprising an N-terminal polypeptide domain having luciferase activity and a C-terminal polypeptide having VAMP1, VAMP2 or VAMP3 activity. Optimising culture conditions to allow for expression of the polypeptide is well within the routine capabilities of a person of skill in the art. In addition, identifying whether or not the chosen culture conditions allow for polypeptide expression is also routine, and the amount of polypeptide expression may be detected using standard techniques such as ELISA or western blotting.

Cells are grown or cultured in the manner with which the skilled worker is familiar, depending on the host cell. The culture medium (also called "growth medium", "medium" or "media" herein) to be used must suitably meet the requirements of the cells in question. Preferably, the culture media is sufficient to support the growth of the host cell. Descriptions of suitable culture media for various cells can be found in the textbook "Culture of Animal Cells: A Manual of Basic Technique and Specialized Applications, Sixth Edition, R. Ian Freshney, 2010 John Wiley & Sons, Inc." By way of example only, SiMa neuroblastoma cells are preferably cultured under the following conditions: SiMa cells (from DSMZ cell collection) are grown in RPMI media supplemented with 10% Fetal Bovine Serum. For differentiation, plates were pre-coated with 10 µg/ml laminin. SiMa cells were seeded at a density of $1 \times 10^4$ cells per well in 96-well plates or $2 \times 10^4$ cells per well in 48-well plates and incubated for 72 hours in differentiation medium (RPMI, B27 or GS21 supplement, 1 mM HEPES and 1% NEAA with 10 µM AT-retinoic acid).

Genetically modified cells may be grown in a liquid medium comprising one or more of a carbon source, usually in the form of sugars, a nitrogen source, usually in the form of organic nitrogen sources such as yeast extract or salts such as ammonium sulfate, inorganic salts, trace elements such as salts of iron, manganese and magnesium and, if appropriate, vitamins, at temperatures of between 0° C. and 100° C., preferably between 25° C. and 40° C., while gassing in carbon dioxide.

Preferred carbon sources are sugars, such as mono-, di- or polysaccharides. Examples of carbon sources are glucose, carbon dioxide, sodium bicarbonate, bicarbonate, fructose, mannose, galactose, ribose, sorbose, ribulose, lactose, maltose, sucrose, raffinose, starch or cellulose. Preferably, the carbon source is carbon dioxide. Alternatively, the carbon source is bicarbonate. The addition of mixtures of a variety of carbon sources may also be advantageous.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as corn steep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassium hydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The culture media used according to the invention may also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

The pH of the liquid medium can either be kept constant, that is to say regulated during the culturing period, or not.

An overview of known cultivation methods can be found in the textbook by Chmiel (Bioprozeßtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Brunswick/Wiesbaden, 1994)).

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature will vary depending on the particular experiment and the host cell. The culture temperature is normally between 15° C. and 45° C., preferably at from 25° C. to 40° C., more preferably at from 25 to 37° C. and may be kept constant or may be altered during the experiment. By way of example only, for SiMa neuroblastoma cells, the temperature is preferably at from 25 to 40° C. and more preferably at 37° C.

The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of vector it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until expression of the polypeptide has occurred. This aim is normally achieved within 6 to 96 hours.

The culture conditions in step (b) are in the presence of the test sample and are such that they allow for neurotoxin-induced cleavage of the polypeptide comprising an N-terminal polypeptide domain having luciferase activity and a C-terminal polypeptide having VAMP1, VAMP2 or VAMP3 activity. In other words, the culture conditions are such that, if a functional neurotoxin were present in the test sample, at least some neurotoxin-induced cleavage of the polypeptide would occur. Optimising culture conditions to allow for neurotoxin-induced cleavage of the polypeptide is well within the routine capabilities of a person of skill in the art. In addition, identifying whether or not the chosen culture conditions allow for neurotoxin-induced cleavage of the polypeptide is also routine, and the amount of neurotoxin-induced cleavage of the polypeptide may be detected using standard techniques such as ELISA or western blotting (as discussed elsewhere).

In one embodiment, culturing steps (a) and (b) are carried out simultaneously. In other words, the test sample may be added to the genetically modified cell at the start of cell culture, or may be added later, once polypeptide expression has already commenced. Optimising the time point at which the genetically modified cell is cultured in the presence of the test sample is well within the routine capabilities of a person of ordinary skill in the art.

Optionally, the test sample is provided in the culture medium.

As described elsewhere, the test sample may comprise a drug product, a food sample, a clinical sample, or an environmental sample, or any combination thereof. Alternatively, the test sample may comprise a tetanus toxoid, or a botulinum toxoid, or a combination thereof.

The test sample may comprise tetanus neurotoxin, botulinum neurotoxin type B, botulinum neurotoxin type D, botulinum neurotoxin type F, botulinum neurotoxin type G, or any combination thereof. For the avoidance of doubt, neurotoxins in the test sample may be naturally occurring neurotoxins, or may be modified (e.g. artificially modified, including chimeras) versions thereof.

The methods provided herein comprise step (c), i.e. determining the level of neurotoxin-induced cleavage of the polypeptide, wherein detection of neurotoxin-induced cleavage of the polypeptide is indicative of neurotoxin activity; and wherein the neurotoxin activity is selected from the group consisting of: tetanus neurotoxin activity, botulinum type B neurotoxin activity, botulinum type D neurotoxin activity, botulinum type F neurotoxin activity and botulinum type G neurotoxin activity, or any combination thereof.

The level of neurotoxin-induced cleavage of the polypeptide may be determined (or detected) using any of the suitable standard techniques discussed elsewhere herein (e.g. ELISA, western blotting, live cell imaging etc).

As used here, "detection" of neurotoxin-induced cleavage encompasses any level or amount of neurotoxin-induced cleavage that is detectable, e.g. visible, quantifiable etc. By way of example, this includes cleavage of at least 1%, 2%, 3%, 4%, 5%, 10%, 15%, 20%, 25%, 30%, 40%, 50%, 60%, 70%, 80%, 85%, 90%, 95% or 100% of the substrate (polypeptide of the invention) at the point of testing (where the point of testing may be, for example, 6 or more hours after the addition of the test sample to the cells. Other examples of suitable time points (e.g. "point of testing" as used above) after the addition of the test sample to the cells include at least 24, 48 hours or 72 hours.

"Neurotoxin-induced cleavage" refers to the cleavage of a polypeptide of the invention, wherein the cleavage is due to the activity of a neurotoxin (i.e. this does not include cleavage of the polypeptide due to other mechanisms such are non-specific polypeptide degradation or cleavage by other non-neurotoxin enzymes). Neurotoxin-induced cleavage may be identified using standard techniques in the art, such as ELISA or the size of the cleavage products (e.g. on a western blot) to confirm that neurotoxin-induced cleavage has occurred. The detection of neurotoxin-induced cleavage of the polypeptide is indicative of neurotoxin activity (e.g. the level or amount of cleavage is proportional to the level or amount of neurotoxin activity in the test sample). In the context of the invention, the terms "neurotoxin-induced cleavage" and "neurotoxin activity" can be used interchangeably.

In certain embodiments of the invention, it may be advantageous to use a negative control (as detailed above). For example, the level of neurotoxin induced cleavage of the polypeptide may be determined and then compared to the level of cleavage of the polypeptide in a negative control sample or with a predetermined reference level for cleavage of the polypeptide, wherein an increased level of cleavage in the presence of the test sample compared to the control sample or compared to the predetermined reference level identifies the presence of neurotoxin-induced cleavage. Negative controls include culturing the same cell under the same conditions in the absence of a test sample or in the presence of a sample that is known to lack neurotoxin activity e.g. a heat inactivated test sample.

Additionally, or alternatively, it may be advantageous to use a positive control (for example to ensure that false negatives are not generated when testing for residual neurotoxin activity of toxoids). An example of a positive control may be culturing the same cell under the same conditions in the presence of a test sample known to comprise functional neurotoxin.

In certain embodiments, it may be advantageous to use an antibody that is specific to the neurotoxin cleavage product of interest. Examples of such antibodies are described elsewhere herein (see also FIG. 5 and corresponding figure legend).

The development and use of other appropriate positive and negative controls is well within the routine capabilities of a person of skill in the art.

Kits

Kits for detecting neurotoxin activity are also provided herein, wherein the kit comprises (a) a nucleic acid molecule encoding a polypeptide comprising an N-terminal polypeptide domain having luciferase activity and a C-terminal polypeptide domain having VAMP1, VAMP2 or VAMP3 activity; and (b) a positive control for detecting neurotoxin activity, wherein the positive control is capable of cleaving the polypeptide encoded by the nucleic acid molecule of (a).

The neurotoxin activity may be selected from the group consisting of: tetanus neurotoxin activity, botulinum type B neurotoxin activity, botulinum type D neurotoxin activity, botulinum type F neurotoxin activity and botulinum type G neurotoxin activity, or any combination thereof.

The nucleic acid molecule of (a) (and the encoded polypeptide) has been described in detail elsewhere herein.

Suitably, the nucleic acid molecule may be part of an expression vector and/or may be within (e.g. form part of; be present in) a genetically modified cell (e.g. a genetically modified SiMa neuroblastoma cell). Expression vectors and genetically modified cells comprising such nucleic acid molecules are also described in detail herein.

The kit provided herein further comprises a positive control for detecting neurotoxin activity, wherein the positive control is capable of cleaving the polypeptide encoded by the nucleic acid molecule of (a).

In one embodiment, the positive control may comprise an appropriate amount of at least one of tetanus neurotoxin, botulinum neurotoxin type B, botulinum neurotoxin type D, botulinum neurotoxin type F and botulinum neurotoxin type G. As described elsewhere herein, the neurotoxin may be naturally occurring or a modified version thereof, wherein the modified version retains neurotoxin activity.

Optionally the kit further comprises reagents for the detection of luciferase activity. Suitable reagents are well known in the art and include but are not limited to luciferin, furimazine, coelenterazine, ATP and other known luciferase substrates [Beyond D-luciferin: expanding the scope of bioluminescence imaging in vivo. Adams S T Jr, Miller S C. Curr Opin Chem Biol. 2014 August; 21:112-20].

The kits may include any or all of the following: assay reagents, buffers, and selective binding partners for one or more of the cleaved polypeptide fragments, all of which can be housed in a container suitable for transport. The selective binding partners may include antibodies that selectively bind to one of the cleaved polypeptide fragments. Examples of such antibodies are described elsewhere herein (see also FIG. 5 and corresponding figure legend).

In some embodiments, the kits include the selective binding partners on a continuous solid surface. An exemplary kit includes a container having a detection binding partner and a positive control for detecting neurotoxin activity.

In addition, the kits may include instructional materials containing directions (i.e., protocols) for the use of the materials provided in the kit. While the instructional materials typically comprise written or printed materials, they may be provided in any medium capable of storing such instructions and communicating them to an end user. Suitable media include, but are not limited to, electronic storage media (e.g., magnetic discs, tapes, cartridges, chips) and optical media (e.g., CD ROM). The media may include addresses to internet sites that provide the instructional materials. Such instructions may be in accordance with any of the methods or uses detailed herein.

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1 94); and Hale and Marham, The Harper Collins Dictionary of Biology, Harper Perennial, NY (1991) provide those of skill in the art with a general dictionary of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a", "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Aspects of the invention are demonstrated by the following non-limiting examples.

EXAMPLES

By genetically engineering the VAMP2 molecule, the inventors have shown that degradation of neurotoxin-cleaved VAMP2 can be prevented. To demonstrate the feasibility of such approach, the inventors have introduced green fluorescent protein GFP-VAMP2 chimeric protein into SiMa neuroblastoma cells using viral transduction (FIGS. 1A and B).

The inventors observed that GFP-VAMP2 localises in vesicles as expected (FIG. 1C, top). Next the inventors transfected mCherry-labelled tetanus light chain (VAMP2-cleaving domain) into SiMa cells (FIG. 1C, lower right). Two days posttransfection, the inventors detected redistribution of the GFP-VAMP2 cleaved product into the cytosol in tetanus-expressing cells (FIG. 1C, lower left). Importantly, immunoblotting revealed a stable GFP-VAMP2 cleaved product opening the possibility for us to quantify tetanus action in vitro (FIG. 1D). These results suggest that it is possible to engineer a cell line with faithful reproduction of all steps of TNx action: binding, translocation and VAMP2 cleavage. One further benefit of the engineered cell line will be its potential utility for testing botulinum toxoids, which are used for immunisation of livestock (6) or in production of botulinum medicines based on type B, D, F and G botulinum neurotoxins. Of note, previously an appearance of cleaved GFP-VAMP2 or VAMP3 products was observed in L6-GLUT4myc myoblasts which were transfected with the tetanus light chain (12).

Figure 2:
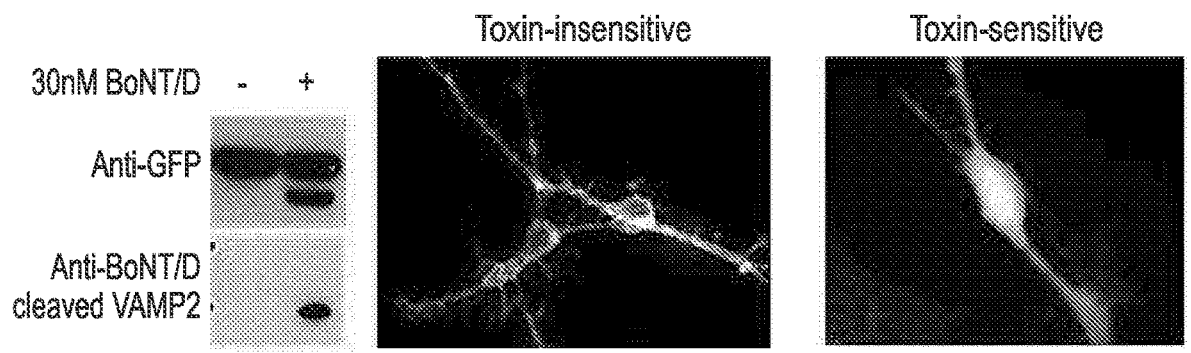
FIG. 2 shows that immortalised mouse neurons are sensitive to botulinum neurotoxin type D evidenced by the appearance of cleaved GFP-VAMP2 product. Note the cleavage of GFP-VAMP2 (blot) and cytosolic transition (right panel) of GFP-VAMP2 in toxin-sensitive cells.

When the inventors transfected GFP-VAMP2 into immortalised mouse neurons they observed release of GFP-VAMP2 product upon treatment with whole botulinum neurotoxin type D (FIG. 2):

Western blot is not viable for high-throughput screening or Quality Control (QC) validation. The released GFP-VAMP2 can be quantified by an ELISA Sandwich immunoassay as was described for detection of cleaved SNAP25 by Botox, a method patented by Allergan (11). Indeed, sandwich ELISA assays, based on two antibodies which bind to different sites on the antigen, are robust, sensitive, and amenable to validation. For the sandwich ELISA one can use enhanced chemiluminescence detection platform which requires additional reporter binding steps (11).

However, the inventors hypothesized that if they replace the GFP molecule with a reporter enzyme they will be able to significantly accelerate detection of VAMP cleavage by removing the final antibody detection steps. The inventors designed antibodies which recognise tetanus- and botulinum-generated fragments of VAMP2, which will allow specific capture of the VAMP2-reporters carrying GFP, luciferase or peroxidase enzymes allowing precise tetanus versus botulinum detection. Generally, application of neurotoxins leads to cleavage of VAMP2 and release of reporter VAMP2 products into the cellular cytosol. This can be confirmed by Western immunoblotting using total or cleaved VAMP2 antibodies. Since Western blots, with intrinsic variability, are difficult to validate, an easy enzymatic read-out for the cell-based assay must be developed for a QC environment. One advantage of the requisite VAMP2-reporters is a possibility of the establishment of cost-effective, high-throughput assays for detection of the cleaved products.

Figure 3:
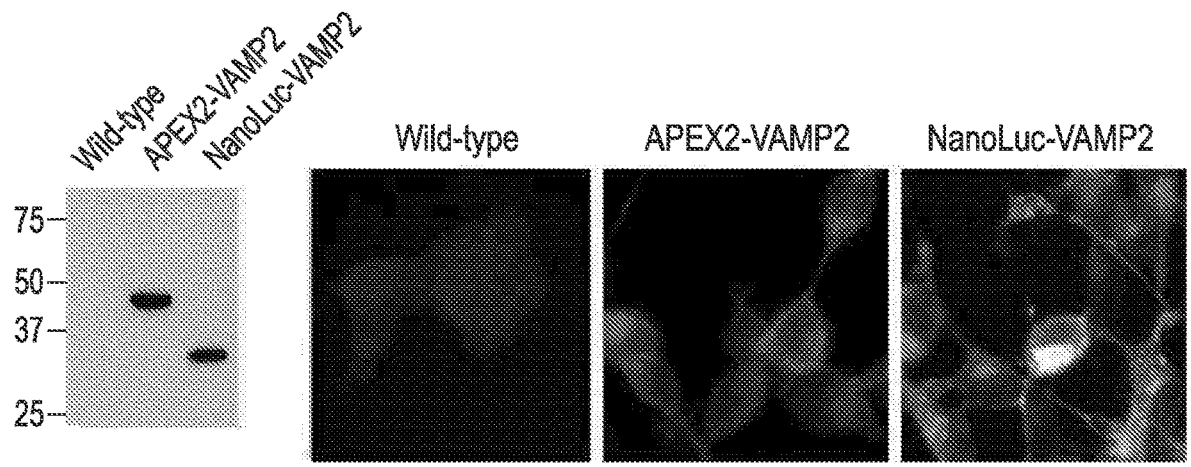
FIG. 3 shows VAMP2 fusions with peroxidase APEX2 (APX2) and luciferase (NanoLuc) are expressed in a stable form in virally-transduced SiMa neuroblastoma cells; both constructs carry an HA-tag (used for immunoblotting, left panel). The fusion proteins localise in vesicular structures as revealed using an HA-tag immunostaining (right panels).

For capture of VAMP molecules cleaved by tetanus and botulinum neurotoxin type B the inventors can use a custom-made VAMP2 antibody which specifically recognizes tetanus-cleaved end of VAMP2 (QAGASQ$_{76}$ (SEQ ID NO: 24)) which can be useful for development of VAMP capture assay. The capture of cleaved VAMP2 fused to an enzyme would allow quantification of the amount of cleaved product in a single step greatly simplifying detection of neurotoxin but this has not been demonstrated in a cell environment. Luciferases are bioluminescent enzymes that catalyse the emission of light through the oxidization of a luciferin. Peroxidases on the other hand provide a variety of detection options, from chromogenic substrates to fluorescence and also luminescence. Both luciferases and peroxidases become very popular in biomolecular imaging and biochemical assay systems prompting development of optimised forms. The inventors prepared fusions of VAMP2 with NanoLuc (optimised luciferase, Promega) and APEX2 (optimised peroxidase) and packaged the plasmids into retroviral vectors. The inventors observed stable expression of these new VAMP2-reporters in SiMa neuroblastoma cells (FIG. 3). Interestingly the inventors found that APEX2-VAMP2 fusion molecule cannot be cleaved by tetanus or botulinum neurotoxins whereas Nluc-VAMP2 exhibited the expected cleavage (FIG. 4).

The inventors quantified sensitivity of SiMa neuroblastoma cells carrying NanoLuc-VAMP2 to BoNT/B and /D by immunoblotting using the total and cleaved VAMP2 antibodies. FIG. 5 demonstrates that detection of botulinum neurotoxins differs depending on the type. Specifically, the inventors could detect cleavage of VAMP by BoNT/B at 300 picomolar whereas sensitivity of SiMa cells for BoNT/D was in the nanomolar range.

Next the inventors prepared 96-well plates coated with VAMP2 antibody recognizing the BoNT/B-cleaved end (QAGASQ$_{76}$ (SEQ ID NO: 24)). The inventors applied Triton X-100-treated SiMa cell extract to these plates for capture of the NanoLuc-VAMP2. The captured reporter enzyme was quantified using NanoGlo reagent (Promega). FIG. 6 shows direct comparison of quantification of NanoLuc-based detection method and Western immunoblotting derived from FIG. 5.

Furthermore, the inventors were able to detect cleavage of NanoLuc-VAMP2 by the tetanus toxin despite poor sensitivity of the SiMa neuroblastoma cells to this clostridial neurotoxin (FIG. 7).

This body of work shows that: (i) it is possible to capture cell-derived botulinum- and tetanus-cleaved VAMP molecules and (ii) fusion with an enzyme not only stabilises the VAMP molecule but also allows highly sensitive readout for high-throughput screening of VAMP-targeting botulinum and tetanus neurotoxins.

It is now possible to transduce NanoLuc-VAMP2 constructs in clostridia-sensitive cell clones for detection of neurotoxin activities. The NanoLuc-VAMP2 constructs have a potential to underpin testing of tetanus products throughout the world. Tetanus vaccine is on the WHO list of essential global medicines and thus potential market size for our cell-based assay could be significant. In 2012, the WHO launched their Global Vaccine Action Plan which aims to bring global immunisation coverage for tetanus by 2020. Major vaccine producers such as GlaxoSmithKline, Sanofi Pasteur and Mass Biologics are committing resources to provide cheaper and larger stocks of common vaccines to developing countries. Thus, replacement of cumbersome animal models with cell-based assays is high on the UK government agenda. Tetanus toxoids and botulinum vaccines are used in livestock farming representing another potential market for our cell-based assays. Our VAMP2-NanoLuc can be utilised also in pharmaceutical production of botulinum-based therapeutics.

By way of a further example of the utility of the invention, FIG. 14 demonstrates that Nanoluc-VAMP2 expressing cells can be used to differentiate potency of novel synthetic versions of BoNT/B.

Materials and Methods

Viral Transduction

Viral pQCXIP plasmids were obtained commercially (Clontech) with the VAMP2 fusion sequences cloned into the NotI and EcorI restriction sites. HEK-293 cells were cultured in DMEM (Life Technologies) with 10% FBS. For packaging of the virus, HEK-293 cells were seeded in 10 cm dishes and grown until 70-90% confluent. Once confluency was reached, cells were washed with PBS and medium was replaced with 6 ml SiMa cell growth medium (RPMI+10% FBS). Cells were then incubated at 37° C. for 2 hours before transfection with viral plasmids. 5.25 µg VAMP2 fusion pQCXIP plasmid, 2.6 µg VSV-G plasmid (viral envelope) and 2.6 µg retroviral Gag-Pol plasmid (group specific antigen and polymerase) were diluted in 400 µl Optimem (Life Technologies) and vortexed. Polyethylenimine (Polysciences) was diluted to 0.13 mg/ml in 400 µl Optimem and this was combined with the DNA followed by a 20 minute incubation at room temperature. The mix was added dropwise to the cells which were then left overnight at 37° C. A further 9 ml of SiMa growth medium was added to the cells which were then incubated for 24 hours at 32° C., 5% $CO_2$.

Supernatant from the HEK-293 cells was collected and mixed with 6 µg/ml polybrene (Sigma) before passing through a 0.45 µm filter syringe. 3 ml of filtered media was added to SiMa cells grown to 50% confluency in 6-well plates, followed by a 20 minute incubation at room temperature. The plate was centrifuged at 2 500 rpm for 90 minutes at room temperature and cells were incubated at 37° C. for 24 hours. Media was replaced with fresh SiMa growth medium and cells were grown for a further 24 hours or until confluency was reached. Cells were expanded into 25 cm$^2$ flasks and cultured in 1 µg/ml puromycin (Sigma) to select for positively transduced cells.

NanoLuc Assay

SiMa cells (DSMZ) and HEK-293 cells (ATCC) were grown at 37° C., 5% $CO_2$. SiMa cells were cultured in RPMI (Life Technologies) supplemented with 10% FBS (Life Technologies). For detection of VAMP2 cleavage, SiMa NLuc-VAMP2 cells were seeded in 48-well plates and differentiated as described previously (Rust et al. 2016). Cells were then treated with toxins at the indicated concentrations and incubated for 72 hours. Following toxin incubation, media was removed and wells were washed once with PBS. Cells were then permeabilised by the addition of 40 µl of Triton X100-based cell extract solution (PBS with 0.5% Triton X-100 and 1× SigmaFast protease inhibitor). Cells were scraped and transferred to tubes on ice where they were incubated for 20 minutes with vortexing every 3-4 minutes. Cell extracts were centrifuged at 14000 rpm, 4° C. for 15 minutes and the supernatant was transferred to a fresh tube for storage at −20° C. until the assay was carried out. 96-well plates pre-coated with Protein A (Thermo-Fisher) were incubated with approximately 3 µg/ml anti-cleaved VAMP2 antibody overnight at 4° C. Wells were washed 3 times with PBS containing 0.05% Tween (PBS-T) followed by blocking with 1% BSA for 1 hour. Wells were again washed three times with PBS-T before addition of cell extracts (15 µl cell extract with 35 µl PBS-T) and incubation at 20° C. for 90 minutes. Following another 3 washes in PBS-T the Nano-Glo substrate (Promega) (2 µl in 50 µl PBS-T) was added to wells and the plate was incubated for 5 minutes in the dark at room temperature. Luminescence was measured using a Fluoroskan Ascent plate reader (Labsystems).

The HA-APEX2-VAMP2 and HA-NanoLuc-VAMP2 were synthesised and cloned into the retroviral expression vector pQCXIP using NotI and EcorI.

REFERENCES

1. Pellizzari R, Rossetto O, Schiavo G, Montecucco C. Tetanus and botulinum neurotoxins: mechanism of action and therapeutic uses. Philos Trans R Soc Lond B Biol Sci. 354:259-68 (1999).
2. Council of Europe. Tetanus vaccine, monographs 0452/0697. European Pharmacopoeia (7th and 8th ed., 2013-14).
3. Behrensdorf-Nicol H A, Weisser K, Krämer B. BINACLE assay for in vitro detection of active tetanus neurotoxin in toxoids. ALTEX 32:137-42 (2015).
4. Sesardic T. Bioassays for evaluation of medical products derived from bacterial toxins. Curr Opin Microb. 15:310 (2012).
5. Davletov, B., Bajohrs, M. and Binz, T. Beyond BOTOX: advantages and limitations of individual botulinum neurotoxins Trends Neurosci 28, 446-552 (2005).
6. Report on botulism in cattle by Advisory committee on the microbiological safety of food (available online at the UK Government Advisory Committee on the Microbiological Safety of Food site at the National Archives link within the Technical Reports section).
7. Hubbard K, Beske P, Lyman M, McNutt P. Functional Evaluation of Biological Neurotoxins in Networked Cultures of Stem Cell-derived Central Nervous System Neurons. J Vis Exp. 96 (2015).
8. Jat P S, Noble M D, Ataliotis P, Tanaka Y, Yannoutsos N, et al. Direct derivation of conditionally immortal cell lines from an H-2Kb-tsA58 transgenic mouse. PNAS USA 88: 5096-5100 (1991).
9. Doran C, Chetrit J, Holley M C, Grundy D, Nassar M A 'Mouse DRG Cell Line with Properties of Nociceptor' PLoS One 10(6):e0128670 (2015).
10. Darios F, Niranjan D, Ferrari E, Zhang F, Soloviev M, Rummel A, Bigalke H, Suckling J, Ushkaryov Y, Naumenko N, Shakirzyanova A, Giniatullin R, Maywood E, Hastings M, Binz T, Davletov B. SNARE tagging allows stepwise assembly of a multimodular medicinal toxin. PNAS USA 107:18197-201 (2010).
11. Fernández-Salas E, Wang J, Molina Y, Nelson J B, Jacky B P, Aoki K R. Botulinum neurotoxin serotype A specific cell-based potency assay to replace the mouse bioassay. PLoS One. 7:e49516 (2012).
12. Randhawa V K et al. VAMP2, but Not VAMP3/Cellubrevin, Mediates Insulin-dependent Incorporation of GLUT4 into the Plasma Membrane of L6 Myoblasts. Mol Biol Cell. 11(7): 2403-2417 (2000).

The invention claimed is:

1. A polypeptide comprising an N-terminal polypeptide domain having luciferase activity and a C-terminal polypeptide domain having VAMP1, VAMP2 or VAMP3 activity.

2. The polypeptide of claim 1, wherein the polypeptide domain having VAMP2 activity comprises the amino acid sequence of SEQ ID NO: 8 or SEQ ID NO: 2, or a conservative amino acid sequence variant thereof.

3. The polypeptide of claim 1, wherein the polypeptide domain having VAMP1 activity comprises the amino acid sequence of SEQ ID NO: 7 or SEQ ID NO: 1, or a conservative amino acid sequence variant thereof.

4. The polypeptide of claim 1, wherein the polypeptide domain having VAMP3 activity comprises the amino acid sequence of SEQ ID NO:9 or SEQ ID NO: 3, or a conservative amino acid sequence variant thereof.

5. The polypeptide of claim 1, wherein the polypeptide domain having luciferase activity comprises the amino acid sequence of SEQ ID NO: 4 or a conservative amino acid sequence variant thereof.

6. A nucleic acid molecule encoding the polypeptide of claim 1.

7. An expression vector comprising the nucleic acid molecule of claim 6.

8. A genetically modified cell comprising the nucleic acid molecule of claim 6, or an expression vector comprising the nucleic acid molecule of claim 6.

9. The genetically modified cell of claim 8, wherein the cell is selected from the group consisting of a SiMa neuroblastoma cell, a LAN5 neuroblastoma cell, a NG108 neuroblastoma cell, an immortalised neuron and a primary neuron.

10. A method of detecting neurotoxin activity in a test sample, comprising:

(a) culturing the genetically modified cell of claim 8 under conditions that allow for expression of a polypeptide comprising an N-terminal polypeptide domain having luciferase activity and a C-terminal polypeptide having VAMP1, VAMP2 or VAMP3 activity;

(b) culturing the cell of (a) in the presence of the test sample under conditions that allow for neurotoxin-induced cleavage of the polypeptide comprising an N-terminal polypeptide domain having luciferase activity and a C-terminal polypeptide having VAMP1, VAMP2 or VAMP3 activity; and (c) detecting neurotoxin-induced cleavage of the polypeptide, wherein detection of neurotoxin-induced cleavage of the polypeptide is indicative of neurotoxin activity;

wherein the neurotoxin activity is selected from the group consisting of: tetanus neurotoxin activity, botulinum type B neurotoxin activity, botulinum type D neurotoxin activity, botulinum type F neurotoxin activity and botulinum type G neurotoxin activity, or any combination thereof.

11. The method of claim 10, wherein culturing steps (a) and (b) are carried out simultaneously.

12. The method of claim 10, wherein the test sample is provided in culture medium.

13. The method of claim 10, wherein the neurotoxin-induced cleavage of the polypeptide is detected by ELISA, immunoblot, or live cell imaging.

14. The method of claim 10, wherein the test sample comprises a drug product, a food sample, a clinical sample, or an environmental sample, or any combination thereof.

15. The method of claim 10, wherein the test sample comprises a tetanus toxoid, or a botulinum toxoid, or a combination thereof.

16. The method of claim 10, wherein when the test sample comprises tetanus neurotoxin, botulinum neurotoxin type B, botulinum neurotoxin type D, botulinum neurotoxin type F, botulinum neurotoxin type G, or any combination thereof, the method detects the level of activity of tetanus neurotoxin, botulinum neurotoxin type B, botulinum neurotoxin type D, botulinum neurotoxin type F, botulinum neurotoxin type G, or any combination thereof, respectively.

17. A kit for detecting neurotoxin activity, comprising:
(a) a nucleic acid molecule encoding a polypeptide comprising an N-terminal polypeptide domain having luciferase activity and a C-terminal polypeptide domain having VAMP1, VAMP2 or VAMP3 activity; and
(b) a positive control for detecting neurotoxin activity, wherein the positive control is capable of cleaving the polypeptide encoded by the nucleic acid molecule of (a).

18. The kit of claim 17, wherein the nucleic acid molecule is part of an expression vector, is within a genetically modified cell, or is part of an expression vector within a genetically modified cell.

19. The kit of claim 18, wherein the genetically modified cell is selected from the group consisting of a genetically modified SiMa neuroblastoma cell, LAN5 neuroblastoma cell, NG108 neuroblastoma cell, immortalised neuron and primary neuron.

20. The kit of claim 17, wherein the kit further comprises reagents for the detection of luciferase activity.

* * * * *